US006900304B2

(12) United States Patent
Tsien et al.

(10) Patent No.: US 6,900,304 B2
(45) Date of Patent: *May 31, 2005

(54) EMISSION RATIOMETRIC INDICATORS OF PHOSPHORYLATION

(75) Inventors: Roger Y. Tsien, La Jolla, CA (US); Alice Y. Ting, La Jolla, CA (US); Jin Zhang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 09/865,291

(22) Filed: May 24, 2001

(65) Prior Publication Data

US 2003/0186229 A1 Oct. 2, 2003

(51) Int. Cl.[7] .................. C12N 15/09; C12N 15/62; C07H 21/04

(52) U.S. Cl. .............. 536/23.4; 424/9.6; 530/350
(58) Field of Search .................. 536/23.4; 424/9.6; 530/350

(56) References Cited

U.S. PATENT DOCUMENTS

| | | | |
|---|---|---|---|
| 4,314,936 | A | 2/1982 | Yaron et al. |
| 5,264,563 | A | 11/1993 | Huse |
| 5,491,084 | A | 2/1996 | Chalfie et al. |
| 5,599,906 | A | 2/1997 | Dasmahapatra |
| 5,602,021 | A | 2/1997 | Davis et al. |
| 5,605,809 | A | 2/1997 | Komoriya et al. |
| 5,614,191 | A | 3/1997 | Puri et al. |
| 5,625,048 | A | 4/1997 | Tsien et al. |
| 5,912,137 | A | 6/1999 | Tsien et al. |
| 5,981,200 | A | 11/1999 | Tsien et al. |
| 5,998,204 | A | 12/1999 | Tsien et al. |
| 6,197,928 | B1 | 3/2001 | Tsien et al. |
| 6,248,550 | B1 | 6/2001 | Tsien et al. |
| 6,656,696 | B2 * | 12/2003 | Craig et al. .................. 435/7.6 |

FOREIGN PATENT DOCUMENTS

| | | |
|---|---|---|
| AU | 717873 | 4/2000 |
| EP | 0 428 000 A1 | 5/1991 |
| EP | 0 877 805 B1 | 5/2002 |
| WO | WO 91/01305 | 2/1991 |
| WO | WO 94/28166 | 12/1994 |
| WO | WO 94/28173 | 12/1994 |
| WO | WO 95/07463 | 3/1995 |
| WO | WO 95/21191 | 8/1995 |
| WO | WO 96/13607 | 5/1996 |
| WO | WO 96/23810 | 8/1996 |
| WO | WO 96/23898 | 8/1996 |
| WO | WO 96/27027 | 9/1996 |
| WO | WO 96/27675 | 9/1996 |
| WO | WO 97/11094 | 3/1997 |
| WO | WO 97/28261 | 8/1997 |
| WO | WO 98/40477 | 9/1998 |
| WO | WO 01/46694 A2 * | 6/2001 ......... G01N/33/542 |

OTHER PUBLICATIONS

Pollard et al. (2002), New Technologies in Exocytosis and Ion Movement, Ann. N.Y. Acad. Sci. 971: 617–619.*
Baird et al., "Circular Permutation and Receptor Insertion within Green Fluorescent Proteins" *Proc. Natl. Acad. Sci., USA*, 96:11241–11246, 1999.
Blumenthal, in "Peptides and Protein Phosphorylation" (Kemp, ed; CRC Press 1990), pp. 135–143.
Chalfie et al., "Green Fluorescent Protein as a Marker for Gene Expression," *Science* 263:802–805 (1994).
Cubitt et al., "Understanding, Improving and Using Green Fluorescent Proteins," *Trends In Biochemical Sciences* 20:448–455 (1995).
Delagrave et al., "Red–Shifted Excitation Mutants of the Green Fluorescent Protein," *Nature Biotechnology* 13(2):151–154 (1995).
Ehrig et al., "Green–Fluorescent Protein Mutants with Altered Fluorescence Excitation Spectra" *FEBS Letters* 367:163–166 (1995).
Geoghegan et al., "Site–Directed Double Fluorescent Tagging of Human Renin and Collagenase (MMP–1) Substrate Peptides Using the Periodate Oxidation of N–Terminal Serine. An Apparently General Strategy for Provision of Energy–Transfer Substrates for Proteases" *Bioconjugate Chemistry* 4(6):537–544 (1993).
Giuliano et al., "Fluorescent Protein Biosensors: Measurement of Molecular Dynamics in Living Cells," *Annual Review of Biophysics and Biomolecular Structure*, 24:405 (1995).
Heim and Tsien, "Engineering Green Fluorescent Protein for Improved Brightness, Longer Wavelengths and Fluorescence Resonance Energy Transfer," *Current Biology* 6(2):178–182 (1996).
Heim et al. "Wavelength Mutations and Posttranslational Autoxidation of Green Fluorescent Protein" *Proceedings of the National Academy of Sciences of USA*, 91:12501–12502 (1994).

(Continued)

*Primary Examiner*—Janet Andres
*Assistant Examiner*—Rachel K. Hunnicutt
(74) *Attorney, Agent, or Firm*—Ginger R. Dreger; James A. Fox; Heller Ehrman White & McAuliffe, LLP.

(57) ABSTRACT

A chimeric phosphorylation indicator is provided. A chimeric phosphorylation indicator can contain a donor molecule, a phosphorylatable domain, a phosphoaminoacid binding domain (PAABD), and an acceptor molecule. A chimeric phosphorylation indicator also can contain a phosphorylatable polypeptide and a fluorescent protein, wherein the phosphorylatable polypeptide is contained within the sequence of the fluorescent protein, or wherein the fluorescent protein is contained within the sequence of the phosphorylatable polypeptide. Also provided are polynucleotides encoding such chimeric phosphorylation indicators, as well as kits containing the indicators or the polynucleotides. In addition, a method of using the chimeric phosphorylation indicators to detect a kinase or phosphatase in a sample is provided.

30 Claims, 7 Drawing Sheets

OTHER PUBLICATIONS

Heim et al., "Improved Green Fluorescence" *Nature* 373:663–664 (1995).

Heim, "Green–Fluorescent Protein Forms for Energy Transfer" *Methods Enzymol.*, 302:408–423 (1999).

Inouye and Tsuji, "*Aequorea* Green Fluorescent Protein: Expression of the gene and fluorescence characteristics of the recombinant protein," *FEBS Letters* 341:2(03):277–280 (Mar. 21, 1994).

Kain et al., "Green Fluorescent Protein as Reporter of Gene Expression and Protein Localization," *Biotechniques* 19(4):650–655 (1995).

Kemp and Pearson, "Protein Kinase Recognition Sequence Motifs" *Trends Biochem. Sci.*, 15:342–346 (1990).

Knight, "Flourimetric Assays of Proteolytic Enzymes" *Methods in Enzymology* 248:18–34 (1995).

Krafft et al., "Synthetic Approaches to Continuous Assays of Retroviral Proteases," *Methods Enzymol.*, 241:70–86 (1994).

Lee et al., "A Requirement of Hydrophobic and Basic Amino Acid Residues for Substrate Recognition by $Ca^{2+}$/calmodulin–dependent protein kinase Ia," *Proc. Natl. Acad. Sci., USA*, 91:6413–6417 (1994).

Matayoshi et al., "Novel Fluorogenic Substrates for Assaying Retroviral Proteases by Resonance Energy Transfer," *Science*, 1990, 247:954.

Meredith et al., "Measurement of Kinase Activation in Single Mammalian Cells," *Nat. Biotechnol.*, 18(3):309–312 (2000).

Mitra et al., "Fluorescence Resonance Energy Transfer between Blue–Emitting and Red–Shifted Excitation Derivatives of the Green Fluorescent Protein," *Gene* 173(1):13–17 (1996).

Nagai et al., "A fluorescent indicator for visualizing cAMP–induced phosphorylation in vivo," *Nat. Biotechnol.*, 18(3):313–316 (2000).

Pearson and Kemp, "Protein Kinase Phosphorylation Site Sequences and Consensus Specify Motifs: Tabulations" *Meth. Enzymol.*, 200:62–81 (1991).

Persechinin et al., "Novel Fluorescent Indicator Proteins for Monitoring Free Intracellular Ca2+" *Cell Calcium*, 22:209–216 (1997).

Roth, "Purification & Protease Susceptibility of the Green–Fluorescent Protein of Aequorea with a Note on Hlistaura" Thesis from the Graduate Program in Biochemistry from Rutgers, the State University of New Jersey (1985).

Schlessinger, "Novel Fluorescent Approaches for Studying Cell Signaling in Single Cells," *Nat. Biotechnol.*, 18(3):262–263 (2000).

Selvin, "Lanthanide–Based Resonance Energy Transfer" *IEEE J. Sel. Top. Quant. Electron*, 2:1077–1087 (1996).

Songyang et al., "Use of an Oriented Peptide Library to Determine the Optimal Substrates of Protein Kinases," *Current Biology*, 4:973–982 (1994).

Tsien et al., "FRET for Studying Intracellular Signalling," *Trends Cell Biol*, 3:242–245 (1993).

Tsien, "The Green Fluorescent Protein" *Ann. Rev. Biochem* 67:509–544 (1998).

Ward et al., "An Energy Transfer Protein in Coelenterate Bioluminescence" *Jour. Biol. Chem.*, 254(3):781–788,) 1979).

Wu and Brand, "Resonance Energy Transfer: Methods and Applications," *Analytical Biochemistry* 218:1–13 (1994).

Yaron et al., "Intramolecularly Quenched Fluorogenic Substrates for Hydrolytic Enzymes," *Analytical Biochemistry*, 95:228–235 (1979).

Confidential (i.e., non–public) communication re. Sato et al. manuscript draft entitled "Fluorescent indicators for imaging protein phosphorylation in single living cells," received by Applicants about, but not before, Jan. 18, 2001. The manuscript was subsequently published in *Nature Biotechnology*, 20:287–294 (Mar. 2002).

\* cited by examiner

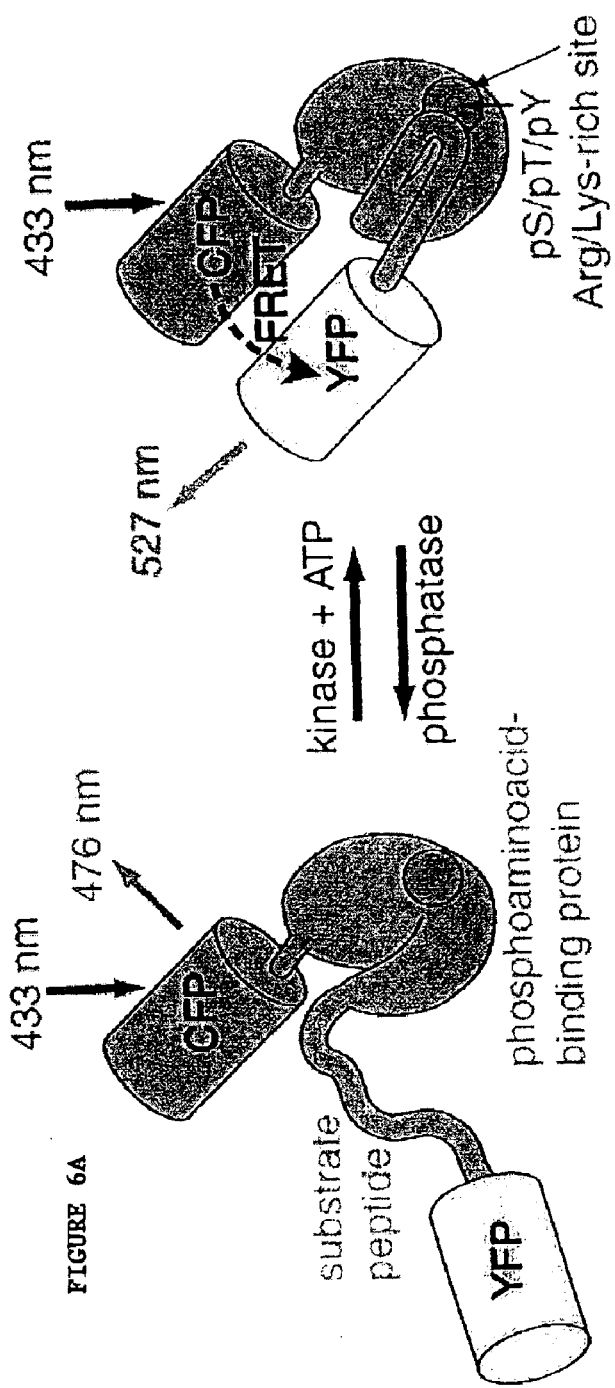
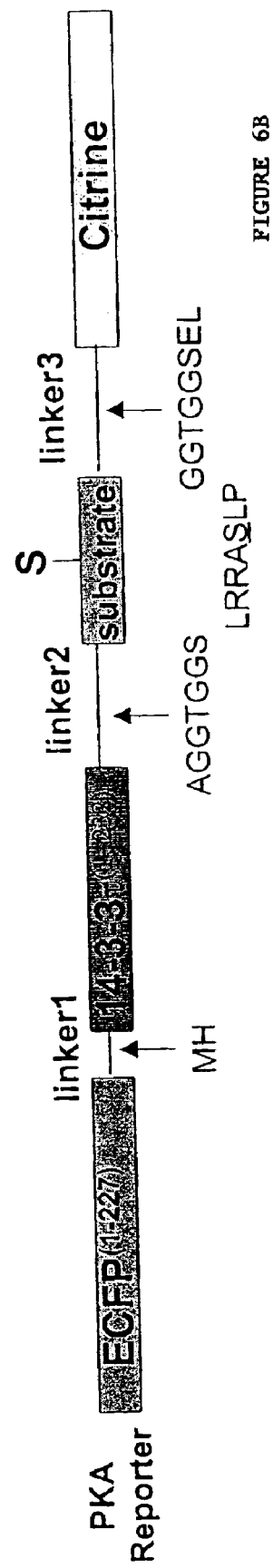
FIGURE 6A
FIGURE 6B

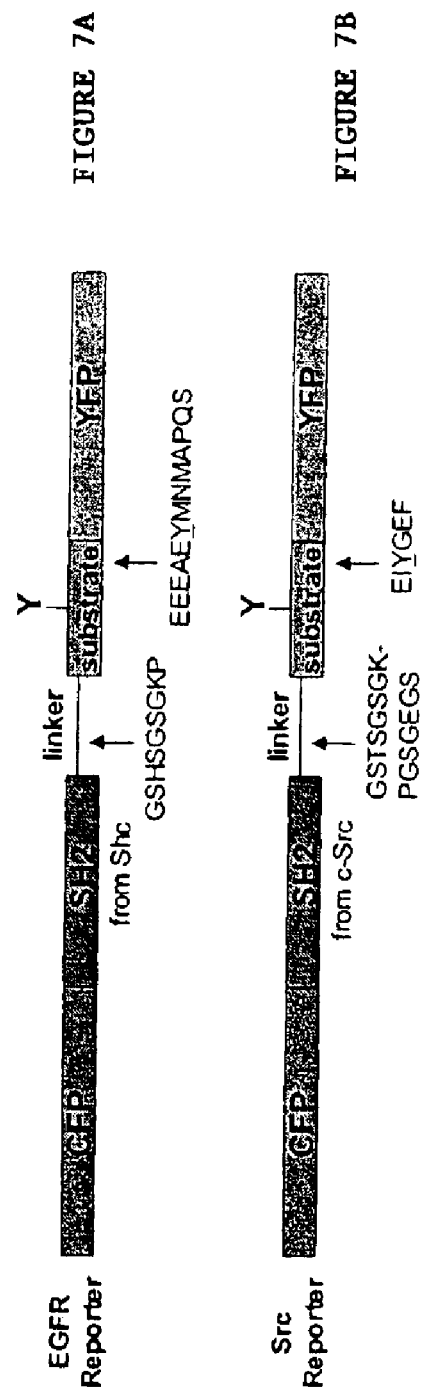

EMISSION RATIOMETRIC INDICATORS OF PHOSPHORYLATION

This invention was made in part with government support under Grant Nos. GM 62114-01 and GM 63443-01 awarded by the National Institute of General Medical Sciences. The government has certain rights in this invention.

BACKGROUND OF THE INVENTION

1. Field of the Invention

The present invention relates generally to reagents for determining kinase and phosphatase activity, and more specifically to chimeric proteins containing two fluorescent proteins and a phosphorylatable domain, and methods of using such chimeric proteins to detect kinase or phosphatase activity.

2. Background Information

Phosphorylation is the most important way that individual proteins are post-translationally modified to modulate their function, while practically all signal transduction involves dynamics of protein-protein interaction. Various technologies have been used to enumerate the main phosphorylation/dephosphorylation events and interacting protein partners involved in cell function, including, for example, function of cardiomyocytes and B lymphocytes. However, the most common currently used technologies such as two dimensional gel electrophoresis, mass spectrometry, co-immunoprecipitation assays, and two-hybrid screens require destroying large numbers of the cells or transferring genes to heterologous organisms. As such, these methods have poor temporal and spatial resolution, and are insufficient to directly probe physiological functions such as contracture or chemotaxis, which occur on the time scale of milliseconds to minutes.

The most widely used method for detecting phosphorylation of specific proteins in single cells utilizes antibodies that discriminate between the phosphorylated and dephosphorylated forms of an antigen. Such antibodies can, in principle, reveal the phosphorylation state of the endogenous protein just prior to the time the cells were fixed for examination, without any introduction of exogenous substrates. However, the identification of antibodies that can discriminate between a phosphorylated and unphosphorylated form of a protein is time consuming and expensive. In addition, the necessary immunocytochemistry is tedious, and is difficult to reassemble into a quantitative time course.

In order to achieve dynamic recording of phosphorylation in single cells, peptides have been labeled with acrylodan, a probe whose fluorescence can be sensitive to the phosphorylation of the peptide. For example, when acrylodan was attached to a peptide from myosin light chain, an approximately 40% decrease in emission peak amplitude upon phosphorylation in vitro was observed. When microinjected into fibroblasts, the peptide incorporated into stress fibers, but no dynamic changes were observable. Substrates for CaMKII and PKA also have been labeled with acrylodan and, after exposure to the kinase, fluorescence was about 200% and 97%, respectively, of initial values. These peptides were hydrophobic enough to stain live cells, and local intensity changes of up to 10% to 20% of initial fluorescence were seen in some regions. The fluorescence of the PKA substrate simultaneously decreased in the cytosol and increased in the nucleus by an amount that was greater than could be explained by the in vitro sensitivity, indicating that more complex factors such as translocation were dominating.

Although no follow-up studies on the use of these acrylodan-labeled peptides have been reported, the approach of developing phosphorylation-sensitive fluorescent substrates may be worth pursuing. However, the use of acrylodan-labeled peptides provides no rational mechanism for phosphorylation sensitivity. Thus, a need exists for phosphorylation-sensitive indicators that can be used to detect phosphorylation or dephosphorylation events in a cell. The present invention satisfies this need and provides additional advantages.

SUMMARY OF THE INVENTION

The present invention relates to a chimeric phosphorylation indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor. The donor molecule or the acceptor or both can be a fluorescent protein, or a luminescent molecule, or a combination thereof. In one embodiment, each of the donor molecule and the acceptor molecule is a fluorescent protein. In another embodiment, one of the donor or acceptor molecule is a luminescent molecule and the other is a fluorescent protein. In a third embodiment, each of the donor molecule and acceptor molecule is a luminescent molecule.

Where a chimeric phosphorylation indicator of the invention contains a fluorescent protein donor molecule, resonance energy transfer can be detected as fluorescence resonance energy transfer (FRET). Where the donor molecule is a luminescent molecule, resonance energy transfer is detected as luminescent resonance energy transfer). Depending on the particular structure of the chimeric phosphorylation indicator as disclosed herein, FRET or LRET can be increased or decreased due to phosphorylation of the indicator by a kinase, and, likewise, can be increased or decreased due to phosphorylation of the indicator by a phosphatase. A change in FRET or LRET can be determined by monitoring the emission spectrum of the acceptor.

A fluorescent protein in a chimeric phosphorylation indictor can be a green fluorescent protein (GFP), a red fluorescent protein (RFP), or a fluorescent protein related to a GFP or an RFP, including a non-oligomerizing fluorescent protein. An RFP, for example, can be a *Discosoma* RFP or a fluorescent protein related to a *Discosoma* RFP such a *Discosoma* DsRed (SEQ ID NO:12) or a mutant thereof (SEQ ID NO:12, including an I125R mutation), or a non-oligomerizing tandem DsRed containing, for example, two RFP monomers operatively linked by a peptide linker. For example, a non-oligomerizing tandem RFP can contain two DsRed (SEQ ID NO:12) monomers or two mutant DsRed-I125R monomers operatively linked by a peptide having an amino acid sequence as set forth as SEQ ID NO:13.

A GFP useful in a chimeric phosphorylation indicator can be an *Aequorea* GFP, a *Renilla* GFP, a *Phialidium* GFP, or a fluorescent protein related to an *Aequorea* GFP, a *Renilla* GFP, or a *Phialidium* GFP. A fluorescent protein related to an *Aequorea* GFP, for example, can be a cyan fluorescent protein (CFP), or a yellow fluorescent protein (YFP), or a spectral variant of the CFP or YFP, including an enhanced GFP (EGFP; SEQ ID NO:4), an enhanced CFP (ECFP; SEQ ID NO:6), an ECFP(1–227) (amino acids 1 to 227 of SEQ ID NO:6), an EYFP-V68L/Q69K (SEQ ID NO:10), or an enhanced YFP (EYFP; SEQ ID NO:8). Furthermore, the fluorescent protein can contain a mutation of an amino acid residue corresponding to A206, L221, F223, or a combination thereof of SEQ ID NO:2, for example, an A206K mutation, an L221K mutation, an F223R mutation, or an L221K and F223R mutation of SEQ ID NO:2; or an A206K mutation, an L221K mutation, an F223R mutation, or an L221K and F223R mutation of SEQ ID NO:6 or SEQ ID NO:10.

A luminescent molecule useful in a chimeric phosphorylation indicator can be, for example, a lanthanide, which can be in the form of a chelate, including a lanthanide complex containing the chelate. Thus, the luminescent molecule can be a terbium ion ($Tb^{3+}$) chelate, for example, a chelate of $Tb^{3+}$ and triethylenetetraamine hexaacetic acid (TTHA), and can further include carbostyril 124 operatively linked to the $Tb^{3+}$ chelate. Where the chimeric phosphorylation indicator is to be contacted with a cell, for example, to detect the presence of a kinase or phosphatase in the cell, the luminescent molecule can further include a membrane translocating domain such as that set forth as SEQ ID NO:18. Such a membrane translocating domain or other molecule to be linked to the luminescent molecule can be operatively linked using, for example, a tetracysteine motif such as that set forth in SEQ ID NO:17.

The phosphorylatable domain in a chimeric phosphorylation indicator of the invention can be any molecule that can be phosphorylated by a specific kinase, for example, a serine/threonine kinase or a tyrosine kinase, or that can contain a phosphate group and can be dephosphorylated by a specific phosphatase. Thus, the phosphorylatable domain can be a synthetic peptide, a peptide portion of a naturally-occurring kinase or phosphatase substrate, a peptidomimetic, a polynucleotide, or the like. By way of example, a serine/threonine kinase domain can include an amino acid sequence as that set forth in SEQ ID NO:20 or SEQ ID NO:32, and a tyrosine kinase phosphorylatable domain can include an amino acid sequence as that set forth in SEQ ID NO:23 or SEQ ID NO:25.

The phosphoaminoacid binding domain (PAABD) in a chimeric phosphorylation indicator of the invention can be an PAABD that specifically binds the particular phosphoaminoacid that is present in the indicator or that can be formed due to phosphorylation of the indicator by a kinase. For example, where the phosphorylatable domain is a serine/threonine kinase domain, the phosphoaminoacid binding domain is selected such that it can bind a phosphoserine or phosphoserine or both, for example, the 14-3-3τ (1–232) peptide. Where the phosphorylatable domain is a tyrosine kinase domain, the phosphoaminoacid binding domain is selected such that it can bind a phosphotyrosine, for example, a Src homology domain-2 (SH2).

A chimeric phosphorylation indicator specific for detecting the presence of a serine/threonine kinase is exemplified herein by a fusion protein containing, in an orientation from the amino terminus to carboxy terminus, an ECFP(1–227) (amino acids 1–227 of SEQ ID NO:6), an MH linker, a 14-3-3τ (1–232) phosphoaminoacid binding domain, an AGGTGGS (SEQ ID NO:19) linker, an LRRASLP (SEQ ID NO:20) phosphorylatable domain, a GGTGGSEL (SEQ ID NO:21) linker, and a citrine. Chimeric phosphorylation indicators specific for detecting the presence of a tyrosine kinase are exemplified herein by an EGFR indicator containing, in an orientation from the amino terminus to carboxy terminus, an ECFP(1–227) (amino acids 1 to 227 of SEQ ID NO:6) molecule, an SH2 phosphoaminoacid binding domain from Shc, a GSHSGSGKP (SEQ ID NO:22) linker, a phosphorylatable domain comprising EEEAEYMNMAPQS (SEQ ID NO:23), and citrine; and by a Src indicator containing, in an orientation from the amino terminus to carboxy terminus an ECFP(1–227) (amino acids 1 to 227 of SEQ ID NO:6), an SH2 phosphoaminoacid binding domain from c-src, GSTSGSGKPGSGEGS (SEQ ID NO:24), a phosphorylatable domain comprising EIYGEF (SEQ ID NO:25), and citrine.

In one embodiment, the specific amino acid that can be phosphorylated by a kinase in the phosphorylatable domain of a chimeric phosphorylation indicator is not phosphorylated, such that the indicator can be used to detect the presence of the kinase in a sample. In another embodiment, the specific amino acid that can be phosphorylated by a kinase in the phosphorylatable domain of a chimeric phosphorylation indicator is phosphorylated, such that the indicator can be used to detect the presence of a phosphatase in a sample. The specific amino acid can be any amino acid that can be phosphorylated by a kinase or dephosphorylated by a phosphatase, for example, serine, threonine, tyrosine, or a combination thereof.

The present invention also relates to a chimeric phosphorylation indicator, which contains a phosphorylatable polypeptide and a fluorescent protein. The specific amino acid that can be phosphorylated by a kinase in the phosphorylatable polypeptide can be unphosphorylated, such that the indicator can be used to detect a kinase activity, or can be phosphorylated, such that the indicator can be used to detect a phosphatase activity.

In one embodiment of a chimeric phosphorylation indicator containing a phosphorylatable polypeptide and a fluorescent protein, the phosphorylatable polypeptide comprises an N-terminal portion and a C-terminal portion, and the fluorescent protein is operatively inserted between the N-terminal portion and C-terminal portion of the phosphorylatable polypeptide. The fluorescent protein can be any fluorescent protein, for example, a GFP, an RFP, or a fluorescent protein related to a GFP or an RFP, and can be in a circularly permuted form. The phosphorylatable polypeptide can be any substrate for a kinase, for example, a tyrosine kinase or a serine/threonine kinase, or for a phosphatase. The fluorescent protein can be operatively inserted into any region of the phosphorylatable polypeptide, for example, in a hinge region or a turn, provided the ability of the polypeptide to act as a substrate is not disrupted.

In another embodiment, a chimeric phosphorylation indicator containing a phosphorylatable polypeptide and a fluorescent protein further contains a phosphoaminoacid binding domain operatively linked to the phosphorylatable polypeptide, wherein the fluorescent protein comprises an N-terminal portion and a C-terminal portion, and wherein the phosphorylatable polypeptide and operatively linked phosphoaminoacid binding domain is operatively inserted between the N-terminal portion and C-terminal portion of the fluorescent protein. The fluorescent protein can be any fluorescent protein, including, a GFP, an RFP, or a fluorescent protein related to a GFP or an RFP. For example, the fluorescent protein can be an EYFP, and the phosphorylatable polypeptide and operatively linked phosphoaminoacid binding domain can operatively inserted between an amino acid sequence corresponding to amino acid positions 145 and 146 of the EYFP or can be substituted for amino acid 145.

The present invention also relates to polynucleotide encoding chimeric phosphorylation indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor. In addition, the present invention relates to a polynucleotide encoding a chimeric phosphorylation indicator containing a phosphorylatable polypeptide and a fluorescent protein, wherein the phosphorylatable polypeptide includes an N-terminal portion and a C-terminal portion, and the fluorescent protein is operatively inserted between the N-terminal portion and C-terminal portion of the phosphorylatable polypeptide. The present invention further relates to a polynucleotide encoding a chimeric phosphorylation indicator containing a phosphoaminoacid binding domain operatively linked to a phosphorylatable polypeptide and a fluorescent protein, wherein the fluorescent protein includes an N-terminal portion and a C-terminal portion, and wherein the phosphorylatable polypeptide and operatively linked phosphoaminoacid binding domain is operatively inserted between the N-terminal portion and C-terminal portion of the fluorescent protein.

Also provided is a vector containing a polynucleotide of the invention, including an expression vector, as well as host cells that contain a polynucleotide of the invention or a vector containing such a polynucleotide. In one embodiment, a polynucleotide of the invention is operatively linked to an expression control sequence, for example, a transcription regulatory element, a translation regulatory element, or a combination thereof. In another embodiment, the polynucleotide is operatively linked to a nucleotide sequence encoding a membrane translocating domain or a cell compartmentalization domain.

The present invention also relates to kits, which contain at least one chimeric phosphorylation indicator of the invention, or a polynucleotide encoding such an indicator. A kit of the invention also can contain a plurality of different chimeric phosphorylation indicators, or of encoding polynucleotides, as well as a combination thereof. Where a kit contains a plurality of different chimeric phosphorylation indicators, the different indicators can contain different phosphorylatable domains, or different donor molecules or acceptor molecules or both, or different fluorescent proteins, as appropriate to the chimeric phosphorylatable indicator. Where a kit contains a polynucleotide encoding a chimeric phosphorylatable indicator, the polynucleotide can be in a vector, or in a host cell, or can be operatively linked to one or more expression control sequences. Where a kit contains a plurality of different polynucleotides, the polynucleotides can encode a different chimeric phosphorylation indicator, or each can contain different expression control sequences, or be contained in different vectors, particularly different expression vectors.

The present invention further relates to a method for detecting a kinase or phosphatase in a sample. In one embodiment, a method of the invention is performed, for example, contacting the sample with a chimeric phosphorylatable indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor; exciting the donor molecule; and determining a fluorescence or luminescence property in the sample, wherein the presence of a kinase or phosphatase in the sample results in a change in the degree of FRET or LRET, thereby detecting the kinase or phosphatase in the sample. The change in the degree of FRET or LRET can be an increased amount of FRET or LRET, or can be a decreased amount of FRET or LRET, and the change can be indicative of the presence of a kinase in the sample, or, where the phosphorylatable domain is phosphorylated prior to contacting the sample with a chimeric phosphorylatable indicator, can be indicative of a phosphatase in the sample.

In another embodiment, a method for detecting a kinase or phosphatase in a sample is performed by contacting the sample with a chimeric phosphorylatable indicator containing a phosphorylatable polypeptide and a fluorescent protein, determining a fluorescence property in the sample, wherein the presence of kinase or phosphatase activity in the sample results in a change in the fluorescence property as compared to the fluorescent property in the absence of a kinase or phosphatase activity, thereby detecting the kinase or phosphatase in the sample. The chimeric phosphorylation indicator can containing a phosphorylatable polypeptide that includes an N-terminal portion and a C-terminal portion, such that the fluorescent protein is operatively inserted between the N-terminal portion and C-terminal portion of the phosphorylatable polypeptide; or the chimeric phosphorylation indicator can contain a phosphoaminoacid binding domain operatively linked to a phosphorylatable polypeptide, which is operatively inserted between an N-terminal portion and a C-terminal portion of the fluorescent protein.

The sample to be examined for kinase activity can be any sample, including, for example, a sample containing a synthetic product to be examined for kinase or phosphatase activity. In one embodiment, the sample is a biological sample, which can be cell, tissue or organ sample, or an extract of such a sample. In another embodiment, the method is performed on an intact cell, which can be in cell culture or can be in a tissue sample. For such a method, the chimeric phosphorylatable indicator can contain a targeting sequence such as a cell compartmentalization domain that can target the chimeric phosphorylatable indicator to cytosol, endoplasmic reticulum, mitochondrial matrix, chloroplast lumen, medial trans-*Golgi cisternae*, a lumen of a lysosome, or a lumen of an endosome. A membrane translocating domain can be a particularly useful cell compartmentalization domain is a membrane translocating domain, which can facilitate translocation of the chimeric phosphorylation indicator into an intact cell.

The phosphorylatable polypeptide in a chimeric phosphorylation indicator comprising a fluorescent protein and a phosphorylatable polypeptide can be unphosphorylated or phosphorylated at an amino acid position specific for a kinase or a phosphatase, depending on whether the method is for detecting a kinase or phosphatase. A method of the invention also can be used to detect an absence of kinase or phosphatase activity in the sample, for example, due to the presence of a kinase inhibitor or phosphatase inhibitor.

The present invention also relates to a method for detecting a kinase inhibitor or phosphatase inhibitor. Such a method can be performed, for example, by determining a first fluorescence property of a chimeric phosphorylatable indicator in the presence of a kinase or a phosphatase, contacting the chimeric phosphorylatable indicator with a composition suspected of being a kinase inhibitor or a phosphatase inhibitor, determining a second fluorescence property of a chimeric phosphorylatable indicator in the presence of the composition, wherein a difference in the first fluorescence property and second fluorescence property identifies the composition as a kinase inhibitor or phosphatase inhibitor. Such a method is particularly adaptable to high throughput screening methods and, therefore, provides a means to screen libraries of compounds to identify a composition that acts as a kinase inhibitor or a phosphatase inhibitor. Accordingly, the present invention also provides a kinase inhibitor or a phosphatase inhibitor identified by such method.

BRIEF DESCRIPTION OF THE DRAWINGS

FIG. 1A illustrates a CFP-PAABD-substrate-YFP chimeric reporter protein, in which phosphorylation of the substrate can increase FRET.

FIG. 1B illustrates a CFP-substrate-YFP-PAABD chimeric reporter protein, in which phosphorylation can decrease FRET.

FIG. 1C illustrates a YFP(1–144)-peptide-PAABD-YFP (146–238) chimeric reporter protein, in which phosphorylation can modulate the YFP protonation state and emission intensity (shown here as an increase).

FIG. 2A shows the SH2 domain from phospholipase C-γ complexed to a phosphopeptide (D-(pY)-IIPLPD; SEQ ID NO:14) from PDGF receptor (Pascal et al., *Cell* 77:461–472, 1994, which is incorporated herein by reference). This mitten-shaped SH2 domain was the model for the PAABD shown in FIG. 1.

FIG. 2B shows the PTB domain from Shc complexed with a phosphopeptide HIIENPQ-(pY)-F (SEQ ID NO:15) from TrkA (Zhou et al., *Nature* 378:584–592, 1995, which is incorporated herein by reference).

FIG. 2C shows the 14-3-3ζ domain complexed with the phosphopeptide ARSH-(pS)-YPA (SEQ ID NO:16; Yaffe et al., *Cell* 91:961–971, 1997, which is incorporated herein by reference).

FIG. 4A shows GFP fused to X and the coral RFP fused to Y. Proximity of X and Y promotes fluorescence resonance energy transfer (FRET) from GFP to RFP.

FIG. 4B shows a terbium chelate ("Tb$^{3+}$ chelate"), with a carbostyril antenna ("carbostyril"), attached to X via a biarsenical ligand ("biarsenical"), binding to a "tetracysteine motif" fused to or inserted within X. Proximity of X and Y promotes luminescence resonance energy transfer (LRET) from Tb$^{3+}$ to RFP. Detailed structures of the chelate, antenna, and ligand are provided in FIG. 5A (note that they are much smaller (1.4 kDa total) than GFP (27 kDa)). In-pointing and out-pointing arrows are as in FIG. 1.

FIG. 5A provides a detailed structure of the carbostyril 124-Tb$^{3+}$-triethylenetetraaminehexaacetic acid biarsenical ligand (TTHA)-Antennapedia peptide conjugate for intracellular labeling in live cells of proteins engineered to contain a tetracysteine motif (-Cys-Cys-X-X-Cys-Cys-; SEQ ID NO:17; Griffin et al., *Science* 281:269–272, 1998, which is incorporated herein by reference). The constituent units corresponding to those indicated in FIG. 4B. After passive internalization mediated by the membrane translocating peptide (SEQ ID NO:18), the latter is released by S—S bond cleavage in the reducing environment of the cytosol (Derossi et al., *Trends Cell Biol.* 8:84–87, 1998, which is incorporated herein by reference). The tetracysteine motif displaces two molecules of 1,2-ethanedithiol, which is membrane-permeant.

FIG. 5B shows the spectral overlap between carbostyril 124-Tb$^{3+}$-TTHA emission (dotted curve, from Li and Selvin, *J. Am. Chem. Soc.* 117:8132–8138, 1995, which is incorporated herein by reference) and coral RFP excitation and emission (solid and dash-dotted curves, respectively). The spikes in the solid and dash-dotted curves near 560 nm and 580 nm are scattering artifacts. As desirable for LRET, the dotted trace overlaps well with the solid trace, but very little with the dash-dotted trace.

FIGS. 6A and 6B illustrate the ratiomeric indicator for visualizing serine/threonine phosphorylation.

FIG. 6A illustrates how FRET between GFPs can report phosphorylation and dephosphorylation. The ECFP(1–227) ("CFP"; amino acids 1 to 227 of SEQ ID NO:6) and citrine ("YFP"; SEQ ID NO:10, except containing a Q69M mutation) are shown as cylinders, reflecting their crystal structures. The phosphoaminoacid binding protein is shown, with a circle inside representing the phosphate-binding site rich in Arg and Lys residues (see FIG. 6B). The kinase/phosphatase substrate peptide domain, including linkers, also is indicated. The smaller circle within the phosphate-binding site (larger circle) represents phosphoaminoacids, as indicated. In-pointing and out-pointing arrows with respect to the GFPs indicate excitation (433 nm) and emission (476 nm) maxima, respectively. Upon phosphorylation by protein kinase, the adjacent phosphoaminoacid binding protein binds to the phosphorylated substrate peptide, which changes the efficiency of FRET between the GFP mutants.

FIG. 6B illustrates the domain structure of the PKA reporter, including, from N-terminus to C-terminus, ECFP (1–227) (amino acids 1 to 227 of SEQ ID NO:6), linker 1 (MH), 14-3-3τ (1–232), linker 2 (SEQ ID NO:19), the kemptide substrate (SEQ ID NO:20), linker 3 (SEQ ID NO:21), and citrine.

FIGS. 7A and 7B illustrate the structures of the chimeric EGFR (FIG. 7A) and Src (FIG. 7B) reporter proteins.

FIG. 7A shows, from N-terminus to C-terminus, the enhanced cyan fluorescent protein (CFP) domain, the SH2 domain from Shc, a linker peptide (SEQ ID NO:22), the substrate domain, including a peptide portion showing the phosphorylation site (SEQ ID NO:23), and the enhanced yellow fluorescent protein domain (YFP).

FIG. 7B shows, from N-terminus to C-terminus, the enhanced cyan fluorescent protein (CFP) domain, the SH2 domain from c-src, a linker peptide (SEQ ID NO:24), the substrate domain, including a peptide-portion showing the phosphorylation site (SEQ ID NO:25), and the enhanced yellow fluorescent protein domain (YFP).

DETAILED DESCRIPTION OF THE INVENTION

Figure 1:
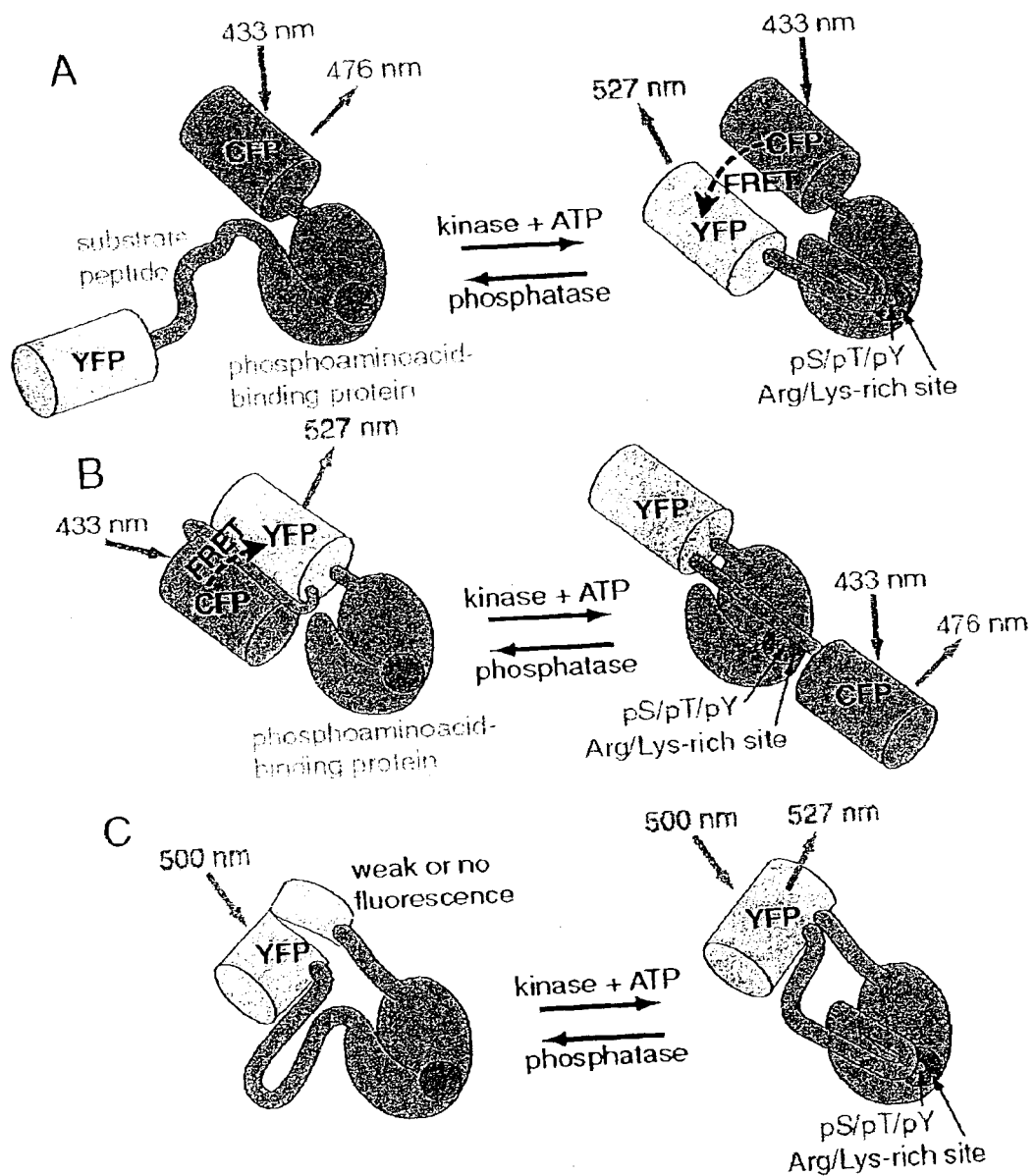
FIGS. 1A to 1C illustrate three generic designs for phosphorylation-specific chimeric reporter proteins, which change fluorescence upon phosphorylation. The fluorescent GFPs, "CFP" and "YFP", are indicated, as are the phosphoaminoacid binding domain (PAABD). The larger circle in the PAABD indicates the phosphate-binding site, which is rich in Arg and Lys residues, and the smaller circle within the larger circle indicates phosphoaminoacids (see FIG. 6B). The kinase/phosphatase substrate peptide also indicated ("substrate peptide"), and includes any spacers present in the construct. In-pointing and out-pointing arrows indicate excitation and emission maxima; respectively, for the GFPs, though the actual spectra are broader than the specific numbers shown in the illustration.

The present invention provides compositions and methods that are generally useful for non-destructively detecting and monitoring protein kinase and phosphatase activities and protein-protein interactions in individual living eukaryotic cells, including mammalian cells, and provide a means to obtain spatial and temporal resolution on the order of a few micrometers and seconds, or better. As disclosed herein, protein kinase and phosphatase activities can be imaged using chimeric substrates (chimeric phosphorylation indicators) that incorporate reporter molecules such as fluorescent proteins or luminescent complexes, whose properties change significantly as a function of the phosphorylation state of the substrate. Protein interactions are detected by resonance energy transfer using fluorescent proteins or lanthanide complexes to label the putative partners. The compositions of the invention are adaptable to modification using methods such as high throughput combinatorial generation and screening techniques and, therefore, readily can be varied to allow monitoring of any desired kinase, phosphatase, or protein interaction. Accordingly, the present invention provides chimeric phosphorylation indicators having various structures as disclosed herein.

In a first embodiment, a chimeric phosphorylation indicator contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor. In a second embodiment, a chimeric phosphorylation indicator contains a phosphorylatable polypeptide and a fluorescent protein. In one aspect of the second embodiment, the phosphorylatable polypeptide comprises an N-terminal portion and a C-terminal portion, and the fluorescent protein is operatively inserted between the N-terminal portion and C-terminal portion of the phosphorylatable polypeptide. In a second aspect of the second embodiment, a phosphoaminoacid binding domain is operatively linked to the phosphorylatable polypeptide, the fluorescent protein comprises an N-terminal portion and a C-terminal portion, and the phosphorylatable polypeptide and operatively linked phosphoaminoacid binding domain is operatively inserted between the N-terminal portion and C-terminal portion of the fluorescent protein. As disclosed herein, the chimeric phosphorylatable indicators of the invention are useful for detecting kinase or phosphatase activity, including in a cell.

Previous techniques for imaging protein heterodimerization in single cells have included observing luminescence resonance energy transfer (LRET) from a lanthanide donor attached to an antibody against one member of the heterodimer to a red dye attached to an antibody against the other partner (Root, *Proc. Natl. Acad. Sci., USA* 94:5685–5690, 1997). This approach has the same advantages and disadvantages as phosphorylation-specific antibodies, including it is applicable to examining endogenous proteins in intact nontransfected tissues, but has poor time resolution and difficulty in generating a continuous time course. Another mode of energy transfer is bioluminescence resonance energy transfer, in which the donor is a luciferase and the acceptor is a GFP (Xu et al., *Proc. Natl. Acad. Sci., USA* 96:151–156, 1999). However, this method has thus far only been demonstrated in bacteria, and the feebleness of bioluminescence will make the technique difficult or impossible to use with single mammalian cells, especially if high spatial or temporal resolution is desired.

Protein complementation assays, in which each potential partner is fused to a fragment of a reporter protein, have a much greater dynamic range between fully interacting and noninteracting states because the reporter enzyme fragments are completely dead before reassembly. In addition, in energy transfer methods, the donor and acceptor do not have to touch each other, and the response is instantaneous, fully reversible, and has minimal effect on the kinetics or affinity of the partners' binding. Such assays also can be complementary to spectroscopic techniques as described below.

FRET-based (cameleon-type) strategies is an established strategy for monitoring certain conformational changes in a natural or chimeric proteins. In a FRET-based strategy, the protein of interest is sandwiched between GFP mutants that are capable of FRET (Tsien, *Ann. Rev. Biochem.* 67:509–544, 1998; Heim, *Meth. Enzymol.* 302:408–423, 1999, each of which is incorporated herein by reference). Changes in conformation of the central protein affect the distance or relative orientation between the flanking GFPs, altering the efficiency of FRET, which can readily be imaged in single cells. This strategy has been successfully employed to monitor 1) protease-mediated cleavage of peptide linkers; 2) $Ca^{2+}$-induced binding of calmodulin to peptides from myosin light chain kinase; 3) $Zn^{2+}$ binding to the $Zn^{2+}$ finger from the transcription factor zif268; 4) cAMP-induced dissociation of the regulatory and catalytic subunits of PKA (Zaccolo et al., *Nat. Cell Biol.* 2:25–29, 2000); 5) cGMP-mediated changes in the conformation of cGMP-dependent protein kinase; and 6) agonist and antagonist binding to nuclear hormone receptors.

As disclosed herein, the FRET strategy has been extended to monitor phosphorylation of a consensus substrate for a kinase (Pearson and Kemp, *Meth. Enzymol.* 200:62–81, 1991; Kemp and Pearson, *Trends Biochem. Sci.* 15:342–346, 1990, each of which is incorporated herein by reference) or phosphatase (Blumenthal, in "Peptides and Protein Phosphorylation" (Kemp, ed; CRC Press 1990), pages 135–143, which is incorporated herein by reference). Such a chimera (FIG. 1A) can include (in order from N-terminus to C-terminus) a GFP mutant such as ECFP, a phosphorylatable domain, a domain capable of binding the phosphoaminoacid in the peptide, and a second GFP mutant such as a pH-insensitive EYFP (see FIG. 1A; see, also, Miyawaki et al., Proc. Natl. Acad. Sci., USA 96:2135–2140, 1999, which is incorporated herein by reference). Phosphorylation of the substrate domain permits the formation of an intramolecular complex with the operatively linked phosphoaminoacid binding domain (PAABD), thereby allowing for an increased FRET between the two fluorescent proteins.

The modular nature of the chimeric phosphorylation indicators facilitates the insertion or substitution of various components, as desired. For example, a *Discosoma* RFP, DsRed, can be substituted for EYFP and ECFP can be substituted with EGFP in the structure exemplified in FIG. 1A. In addition, the ordering of the donor and acceptor molecules can be interchanged, as can the order of the phosphorylatable domain and the PAABD. In addition, the junctions between the components can be varied using peptide linkers such as those exemplified herein to optimize the responsiveness of the indicators.

A fluorescent protein useful in a constructing a chimeric phosphorylation indicator of the invention can be any fluorescent protein, including, for example, a green fluorescent protein (GFP) such as an *Aequorea victoria* GFP, a *Renilla reniformis* GFP, a *Phialidium gregarium* GFP; a red fluorescent protein (RFP) such as a *Discosoma* RFP; or a fluorescent protein related to a GFP or an RFP, such as a cyan fluorescent protein (CFP), a yellow fluorescent protein (YFP), an enhanced GFP (EGFP; SEQ ID NO:4), an enhanced CFP (ECFP; SEQ ID NO:6), an enhanced YFP (EYFP; SEQ ID NO:8), a DsRed fluorescent protein (SEQ ID NO:12), citrine, which has an amino acid sequence as set forth in SEQ ID NO:10, except containing a Q69M mutation; or a mutant or variant of such fluorescent proteins.

A fluorescent protein useful in a constructing a chimeric phosphorylation indicator of the invention also can be a non-oligomerizing fluorescent protein, in which the propensity of the fluorescent protein to oligomerize is reduced or eliminated. The propensity of a fluorescent protein to oligomerize can be reduced or eliminated by operatively linking a first monomer of a fluorescent protein to at least a second monomer of the fluorescent protein, thereby forming an intramolecular 'dimer', 'trimer' or the like. Such operatively linked homopolymers, which have a substantially reduced ability to form intermolecular oligomers, are exemplified by two monomers of DsRed (SEQ ID NO:12) operatively linked by a peptide linker (SEQ ID NO:13), and by two monomers of a mutant DsRed, which has an amino acid sequence of SEQ ID NO:12, and including an I125R mutation, operatively linked by the peptide linker of SEQ ID NO:13. The propensity of a fluorescent protein to oligomerize also can be reduced or eliminated by introducing one or more mutations into the fluorescent protein. Such mutations are exemplified by a mutation of one or a combination of amino acid residues A206, L221 or F223 of *Aequorea* GFP (SEQ ID NO:2), or a mutation of another fluorescent protein that corresponds to a mutation of A206, L221 or F223 of SEQ ID NO:2, for example, by the mutations A206K, L221K, F223R of GFP (SEQ ID NO:2), or by the mutations L221K and F223R of ECFP (SEQ ID NO:6) and EYFP-V68L/Q69K (SEQ ID NO:10), which are spectral variants of *Aequorea* GFP.

*Aequorea* GFP is widely used in cell biology as a protein module that can be fused to host proteins to make the latter fluorescent (Tsien, Ann. Rev. Biochem. 67:509–544, 1998, which is incorporated herein by reference). For example, GFP is commonly used to characterize subcellular localization and trafficking properties of proteins, to which the GFP is fused. In addition, spectral variants of GFP, including CFP and YFP and variants thereof have been used to measure the associative properties of host proteins by FRET. FRET between CFP and YFP also has been exploited to create biosensors for calcium ion, and to determine the associative properties of growth factor receptors and G protein-coupled receptors.

The availability of a wide range of variously-colored "spectral mutants" of GFP has provided a potential means for monitoring the associative properties of proteins via FRET. FRET is a quantum mechanical phenomenon of radiation-less energy transfer between two fluorophores, that is dependent on the proper spectral overlap of a donor and an acceptor, their distance from each other, and the relative orientation of the chromophores' transition dipoles. Using standard molecular biology technology, fusions can be generated between proteins of interest and spectral mutants of fluorescent proteins, which can then serve effectively as donor and acceptor FRET partners. As indicated above, the GFP spectral mutants have most of the requisite properties to serve as useful FRET partners, except for their homoaffinity and propensity for dimerization. Thus, while the number of FRET-based assays using GFP and its variants is increasing (see, for example, Mitra et al., Gene 173:13–17, 1996; Hartman and Vale, Science 286:782–785, 1999; Zacharias et al., Curr. Opin. Neurobiol. 10:416–421, 2000), the propensity of the GFP-related fluorescent proteins to associate with each other can complicate characterization of protein associations reported by FRET, which should be due solely to interactions of the proteins with no participation from the fluorophore to which they are linked.

A luminescent molecule also can be useful in a chimeric phosphorylation indicator. For example, a lanthanide, which can be in the form of a chelate, including a lanthanide complex containing the chelate. Thus, the luminescent molecule can be a terbium ion ($Tb^{3+}$) chelate, for example, a chelate of $Tb^{3+}$ and triethylenetetraamine hexaacetic acid (TTHA), and can further include carbostyril 124 operatively linked to the $Tb^{3+}$ chelate. Where the chimeric phosphorylation indicator is to be contacted with a cell, for example, to detect the presence of a kinase or phosphatase in the cell, the luminescent molecule can further include a membrane translocating domain such as that set forth as SEQ ID NO:18. Such a membrane translocating domain or other molecule to be linked to the luminescent molecule can be operatively linked using, for example, a tetracysteine motif such as that set forth in SEQ ID NO:17.

Lanthanide chelates are ideal donors for luminescence resonance energy transfer (LRET) to RFPs such as DsRed, and provides four major advantages over conventional FRET (Selvin, IEEE J. Sel. Top. Quant. Electron. 2:1077–1087, 1996; Li and Selvin, J. Am. Chem. Soc. 117:8132–8138,1995, each of which is incorporated herein by reference): 1) Because the emission spectrum of lanthanide chelates consists of sharp lines rather than broad peaks, it is easy to separate the donor lanthanide emission from that of any conventional acceptor. 2) Because the LRET-sensitized emission from the acceptor has millisecond kinetics, it can be easily discriminated from directly-excited emission, which has nanosecond kinetics. These two advantages mean that even very low degrees of LRET (i.e., interactions at distances much greater than the Forster distance, Ro) can be detected. 3) The background autofluorescence also has lifetimes in nanoseconds and can likewise be easily eliminated by pulsed excitation and gated detection. Thus, much lower concentrations of probes and labeled proteins should be sufficient. 4) The lanthanide emission is essentially unpolarized, so that the dependences of LRET on the orientations of the donor and acceptor are respectively eliminated and greatly reduced.

A problem with intracellular LRET is that few methods have been established for introducing extremely polar lanthanide chelates into intact cells and site-specifically labeling proteins there. Nonpolar lanthanide chelates such as Tris (3-β-diketonates) are available, but they lack sufficient kinetic stability for use in the presence of intact proteins and cells. Known chelates that are stable enough are extremely hydrophilic polyaminocarboxylates, which have never been demonstrated to cross cell membranes unaided. As such, the lanthanide complexes used in the chimeric phosphorylation indicators of the invention can be conjugated to a membrane translocating peptide such as the Antennapedia hydrophobic signal peptides (Rojas et al., *Nat. Biotechnol.* 16:370–375, 1998, which is incorporated herein by reference), VP22 of herpes virus (Elliot and O'Hare, *Cell* 88:223–233, 1997, which is incorporated herein by reference), or the TAT protein, which can mediate import of protein multimers and large polyanions such as antisense nucleic acids of at least 55 bases (Derossi et al., *Trends Cell Biol.* 8:84–87, 1998, which is incorporated herein by reference).

Figure 5A:
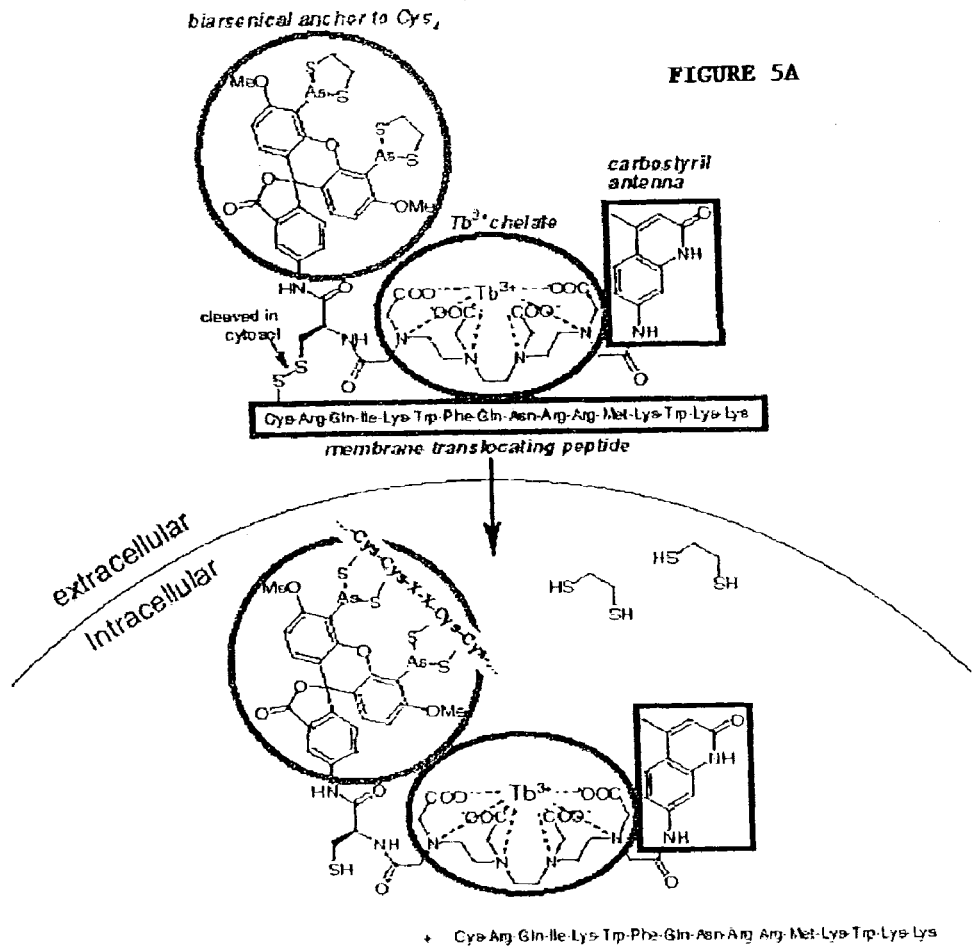
FIGS. 5A and 5B illustrates labeling of live cells using an engineered construct.

The site-specific attachment of the lanthanide chelates to recombinant proteins in intact cells ca be accomplished by linking the lanthanide complex to a biarsenical reagent, which can selectively find and bind a particular tetracysteine motif engineered into a host protein (Griffin et al., *Science* 281:269–272, 1998, which is incorporated herein by reference). Such a structure is exemplified in FIG. 5A, wherein one end of a $Tb^{3+}$ chelate is attached to the sensitizer or antenna chromophore, e.g., a carbostyril dye (Li and Selvin, supra, 1995), and the other end is attached to the biarsenical reagent and the membrane-translocating peptide via the simplest heterotrifunctional linker, L-cysteine. The biarsenical reagent is not a fluorescent dye, as previously described, so that it does not quench or interfere with the sensitizer or $Tb^{3+}$, and such that the fluorescein moiety is methylated twice to force it into the colorless spiro form. The linkage to the membrane-translocating peptide (in this case penetratin-1 from Antennapedia; Derossi et al., supra, 1998) is via a disulfide bond, which will be cleaved in the reducing environment of the cytosol. Thus the translocating peptide will be discarded before the biarsenical unit attaches the $Tb^{3+}$ complex to the tetracysteine-containing host protein.

Figure 5B:
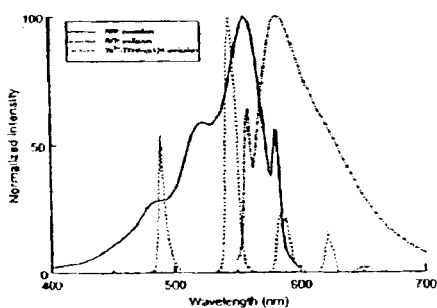

DsRed or a mutant thereof can be an acceptor molecule for LRET from the $Tb^{3+}$ chelate, as the spectral overlap between $Tb^{3+}$ emission and the RFP excitation spectrum is very good (see FIG. 5B). The $Tb^{3+}$ chelate is excited via the carbostyril antenna either with a pulsed nitrogen laser at 337 nm or a mercury-xenon flashlamp at 365 nm. Emissions from both the $Tb^{3+}$ donor and the RFP acceptor are collected in time-resolved manner, which is easy because the relevant time scale is milliseconds. If there is a significant amount of $Tb^{3+}$ donor very far from the RFP acceptor, because either the donor has not found its target protein or the latter is not bound to its partner bearing the RFP, the corresponding emission will have a very long lifetime characteristic of free $Tb^{3+}$ complex. When the $Tb^{3+}$ complex and the RFP are associated, the lifetime of the $Tb^{3+}$ complex is somewhat shortened, whereas the RFP develops a component of similar lifetime. Both components can be quantified, as they are easily separated due to the narrow emission lineshape of the $Tb^{3+}$.

The phosphorylatable domain in a chimeric phosphorylation indicator of the invention can be any molecule that can be phosphorylated by a specific kinase, for example, a serine/threonine kinase or a tyrosine kinase, or that can contain a phosphate group and can be dephosphorylated by a specific phosphatase. Thus, the phosphorylatable domain can be a synthetic peptide, a peptide portion of a naturally-occurring kinase or phosphatase substrate, a peptidomimetic, a polynucleotide, or the like. By way of example, a serine/threonine kinase domain can include an amino acid sequence as that set forth in SEQ ID NO:20 or SEQ ID NO:32, and a tyrosine kinase phosphorylatable domain can include an amino acid sequence as that set forth in SEQ ID NO:23 or SEQ ID NO:25.

The phosphoaminoacid binding domain (PAABD) in a chimeric phosphorylation indicator of the invention can be an PAABD that specifically binds the particular phosphoaminoacid that is present in the indicator or that can be formed due to phosphorylation of the indicator by a kinase. For example, where the phosphorylatable domain is a serine/threonine kinase domain, the phosphoaminoacid binding domain is selected such that it can bind a phosphoserine or phosphoserine or both, for example, the 14-3-3τ (1–232) peptide. Where the phosphorylatable domain is a tyrosine kinase domain, the phosphoaminoacid binding domain is selected such that it can bind a phosphotyrosine, for example, a Src homology domain-2 (SH2).

Figure 2:
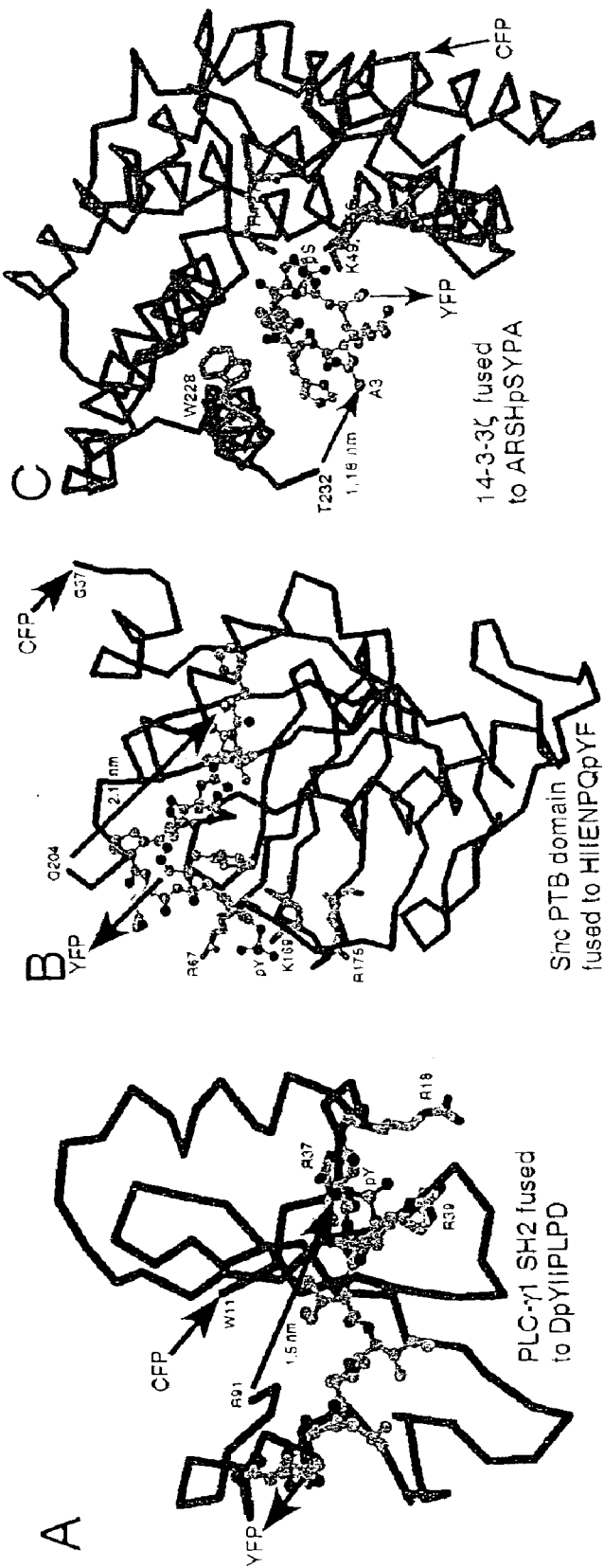
FIGS. 2A to 2C show the structures of various phosphoaminoacid-binding domains complexed to phosphorylated peptides, fused together and bracketed by CFP and YFP to form chimeric indicators as illustrated in FIG. 1A. The dark gray lines represent the protein, with a few key residues involved in binding the peptide shown in stick form, and the phosphopeptide shown in ball-and-stick representation. Heavy arrows indicate linkers that can connect the protein to the peptide or either of them to CFP or YFP (the arrow direction indicates amino to carboxy). The required length in real space of the linker between protein and peptide is indicated. By rearrangement of these linkers (not shown), indicators of the generic structures illustrated in FIGS. 1B and 1C can be constructed analogously.

The SH2 or PTB domains, which bind phosphotyrosine in certain contexts, are the best known and most well understood PAABDs. For example, the NMR structure of an SH2 domain from phospholipase-C-γ complexed with a phosphopeptide from the PDGF receptor (Pascal and Singer, supra, 1994) suggests these two modules can be fused and sandwiched between a donor and acceptor molecule such as CFP and YFP (see FIG. 2A). Similarly, the structure of a PTB domain from She binding a partner peptide from TrkA (Zhou et al., supra, 1995) indicates that these elements also can be used in a chimeric phosphorylation indicator (see FIG. 2B).

Phosphoserine/phosphothreonine binding domains also have been described, including those of the 14-3-3 proteins. For example, 14-3-3ζ recognizes a consensus sequence R(R/K)(F/R/S/N)(R/H/K) pSer (W/Y/F/L)P (SEQ ID NO:42; Yaffe et al., supra, 1997) that can encompass consensus sites for several important protein kinases such as PKA, PKG, and PKC (Pearson and Kemp, supra, 1991; Kemp and Pearson, supra, 1990). FIG. 2C exemplifies of how kinase activity can be reported using a chimeric phosphorylatable indicator comprising a 14-3-3 protein fused to a domain that is phosphorylatable on a Ser residue.

As disclosed herein, PAABDs also can be identified, for example, by screening phage display libraries using binding to immobilized phosphoaminoacids for affinity selection, or can be evolved from known orthophosphate-binding or sulfate-binding proteins, or from phosphatases by reduction of their catalytic activity. A simple example of the latter approach was the replacement of a catalytic aspartate residue in the tyrosine phosphatase, PTP1B, thus converting it into a "substrate-trap", i.e., a high-affinity binder of phosphotyrosine-containing peptides with a very slow hydrolytic rate (Flint et al., *Proc. Natl. Acad. Sci., USA* 94:1680–1685, 1997, which is incorporated herein by reference). It should be recognized that a small residual phosphatase activity can be quite beneficial because it can provide a backup mechanism to gradually reset the chimeric phosphorylation indicator back to the nonphosphorylated state, if it is not a substrate for an endogenous phosphatase.

As disclosed herein, FRET can increase or decrease upon phosphorylation or dephosphorylation of a chimeric phosphorylation indicator. For example, using chimeras of GFP-CaM binding peptide-BFP-permuted CaM, FRET from BFP to GFP was strong in the absence of $Ca^{2+}$, presumably because the CaM-binding peptide was flexible enough to allow the two fluorescent proteins to dimerize, whereas, upon elevation of $Ca^{2+}$, dimerization and FRET were disrupted, perhaps because $(Ca^{2+})_4$-CaM binding forced the peptide into a more extended conformation (Perschini et al., Cell Calcium 22:209–216, 1997, which is incorporated herein by reference). As such, substitution of the CaM-binding peptide and CaM by a phosphorylatable domain and a PAABD can be used to generate sensors in which kinase (or phosphatase) activity decreases FRET (see FIG. 1B), the having an opposite response from the cameleon-type indicators described above (see, also, FIG. 1A). Similarly, the connectivity of the spacers in the structures shown in FIG. 2 can be modified to generate such Perschini-type chimeric phosphorylatable indicators.

The present invention also provides a chimeric phosphorylation indicator containing a phosphorylatable polypeptide and a fluorescent protein. These indicators were modeled on chimeras in which a CaM or a Zn-finger motif was inserted in place of Y145 of EYFP, whereupon binding of $Ca^{2+}$ or $Zn^{2+}$ enhanced the fluorescence by 7 or 1.7-fold respectively (Baird et al., Proc. Natl. Acad. Sci., USA 96:11241–11246, 1999, which is incorporated herein by reference). A GFP with β-lactamase inserted between residues 172 and 173 increased fluorescence −1.5 fold upon addition of β-lactamase-inhibitory protein (Selvin, supra, 1996). The application of this strategy to phosphorylation detection is exemplified in FIG. 1C, wherein a phosphorylatable peptide and PAABD are inserted within position 145 of EYFP. a conformational change in the insert can modulate the fluorescence efficiency of the EYFP reporter. This strategy utilizes only one fluorescent protein, and can give very large responses, including changes in pH-sensitive fluorescence at one wavelength rather than a change in ratio of emissions at two wavelengths.

Accordingly, in one embodiment of a chimeric phosphorylation indicator containing a phosphorylatable polypeptide and a fluorescent protein, a phosphoaminoacid binding domain is operatively linked to the phosphorylatable polypeptide, the fluorescent protein comprises an N-terminal portion and a C-terminal portion, and the phosphorylatable polypeptide and operatively linked phosphoaminoacid binding domain is operatively inserted between the N-terminal portion and C-terminal portion of the fluorescent protein. The fluorescent protein can be any fluorescent protein, including, a GFP, an RFP, or a fluorescent protein related to a GFP or an RFP, and is exemplified by an EYFP in which the phosphorylatable polypeptide and operatively linked phosphoaminoacid binding domain is operatively inserted between amino acid positions 145 and 146 of the EYFP or is substituted for amino acid 145.

Figure 3:
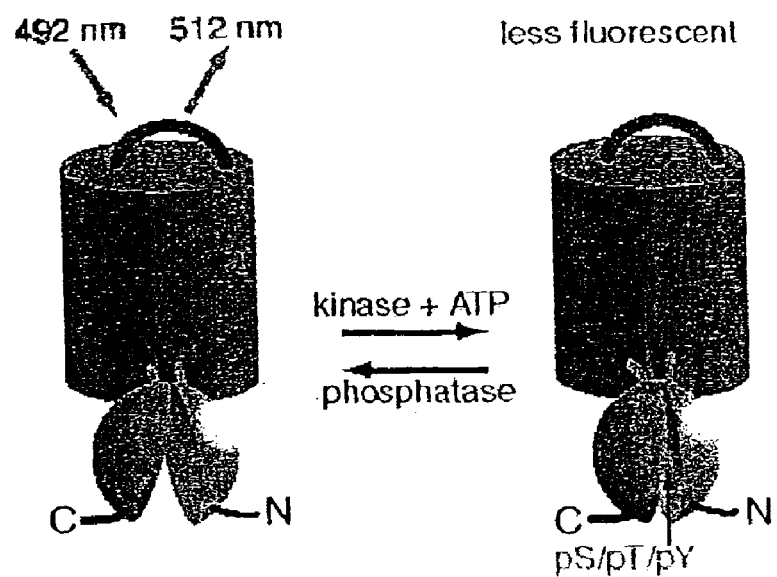
FIG. 3 provides a schematic structure of a circularly permuted GFP (cpGFP; cylinder) inserted within a protein (clamshell) whose conformation changes upon phosphorylation. The tube (arc) at the top of the cpGFP cylinder indicates a spacer linking the original N-terminus and C-terminus of GFP. Linkers connecting the new N-terminus and C-terminus of the cpGFP to the insertion site within the phosphorylatable protein are indicated by tubes. The N-terminus and C-terminus of the chimera are the same as those of the phosphorylatable protein alone, and also are indicated by tubes. The circle in the protein indicates the phosphorylated amino acid. In this example, phosphorylation favors a closed conformation, which pries open a cleft in the cpGFP, diminishing cpGFP fluorescence.
Figure 4:
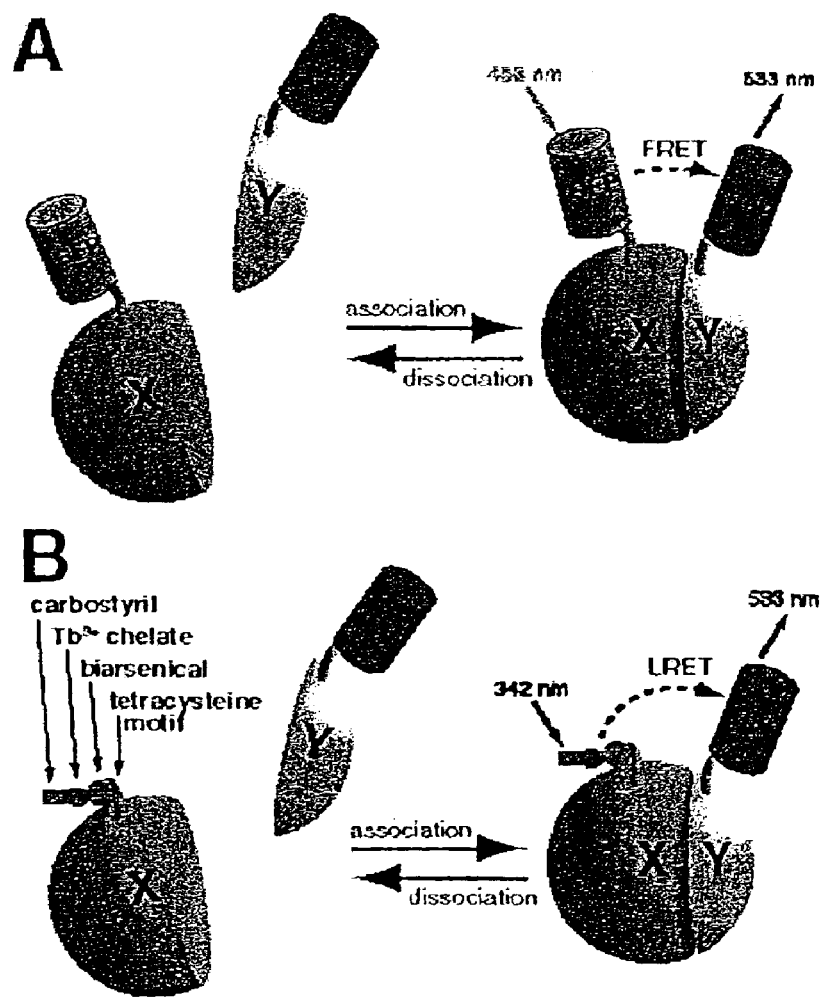
FIGS. 4A and 4B illustrate detection by resonance energy transfer of heterodimer formation between proteins X and Y.

For many kinases and phosphatases, an artificial substrate, which can be operatively linked to PAABDs and a fluorescent protein, may not be a good surrogate for the normal endogenous substrates. As such, a fluorescent protein such as GFP, particularly a circularly permuted GFP (cpGFP), can be operatively inserted into the endogenous substrate, thus generating a chimeric phosphorylation indicator (see FIG. 3). Preferably, the fluorescent protein is inserted at a hinge region or turn, such that phosphorylation can significantly change the local conformation, which is transmitted to the fluorescent protein, thereby modifying its fluorescence as discussed above. Accordingly, in another embodiment of a chimeric phosphorylation indicator containing a phosphorylatable polypeptide and a fluorescent protein, the phosphorylatable polypeptide comprises an N-terminal portion and a C-terminal portion, and the fluorescent protein is operatively inserted between the N-terminal portion and C-terminal portion of the phosphorylatable polypeptide.

Unless specifically indicated otherwise, all technical and scientific terms used herein have the same meaning as commonly understood by those of ordinary skill in the art to which this invention belongs. In addition, any method or material similar or equivalent to a method or material described herein can be. used in the practice the present invention. For purposes of the present invention, the following terms are defined.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" replaces "T."

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a chimeric phosphorylation indicator of the invention linked to a polypeptide of interest such as a cell compartmentalization domain. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-*Golgi cisternae*, or a lysosome or endosome, or is a membrane translocating peptide, which allows a molecule operatively linked thereto to cross a cell membrane and enter an intact cell. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., *EMBO J.* 10:4033–4039, 1991; Buss et al., *Mol. Cell. Biol.* 8:3960–3963, 1988; U.S. Pat. No. 5,776,689, each of which is incorporated herein by reference).

The term "operatively linked" or "in operative linkage" also is used herein to indicate that the components of a chimeric phosphorylation indicator are joined together such that each component maintains its function relevant to phosphorylation detection, or can be induced to express its function. For example, the phosphorylatable domain is operatively linked to the PAABD such that, when an amino acid residue of the phosphorylatable domain is phosphorylated, the PAABD can bind to the phosphoaminoacid. Similarly, the donor molecule and acceptor molecule are in operative linkage, through the phosphorylatable domain and PAABD, as well as any linker molecules, such that, upon excitation of the donor molecule, FRET can occur so as to excite the acceptor, which, in response, fluoresces. Methods for operatively linking the components of a chimeric phosphorylation indicator, including the use of linker and spacer peptides and the like, can be determined rationally based, for example, on crystallographic information, can be extrapolated from the methods and compositions disclosed herein, or can be determined empirically.

The term "operatively inserted" is used similarly herein to refer to the introduction of a first polypeptide into a second polypeptide, at a position between the N-terminus and C-terminus of the second polypeptide, such that each of the polypeptides maintains its original function or can be induced to express its original function. For example, where a phosphorylatable polypeptide is operatively inserted into a fluorescent protein, the phosphorylatable polypeptide maintains its ability to act as a substrate for a phosphatase or kinase, and the fluorescent protein maintains its characteristic fluorescence property, although the fluorescence property may not be exhibited due, for example, to the phosphorylation state of the phosphorylatable polypeptide.

The term "oligomer" refers to a complex formed by the specific interaction of two or more polypeptides. A "specific interaction" or "specific association" is one that is relatively stable under specified conditions, for example, physiologic conditions. Reference to a "propensity" of proteins to oligomerize indicates that the proteins can form dimers, trimers, tetramers, or the like under specified conditions. Generally, fluorescent proteins such as GFPs and DsRed have a propensity to oligomerize under physiologic conditions although, as disclosed herein, fluorescent proteins also can oligomerize, for example, under pH conditions other than physiologic conditions.

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound. The term "label" refers to a composition that is detectable with or without the instrumentation, for example, by visual inspection, spectroscopy, or a photochemical, biochemical, immunochemical or chemical reaction. Useful labels include, for example, phosphorus-32, a fluorescent dye, a fluorescent protein, an electron-dense reagent, an enzymes (such as is commonly used in an ELISA), a small molecule such as biotin, digoxigenin, or other haptens or peptide for which an antiserum or antibody, which can be a monoclonal antibody, is available. It will be recognized that a non-oligomerizing fluorescent protein of the invention, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and isolation of the expressed protein, respectively. A label useful for purposes of the present invention generally generates a measurable signal such as a radioactive signal, fluorescent light, enzyme activity, and the like, either of which can be used, for example, to quantitate the amount of the non-oligomerizing fluorescent protein in a sample.

The term "nucleic acid probe" refers to a polynucleotide that binds to a specific nucleotide sequence or sub-sequence of a second (target) nucleic acid molecule. A nucleic acid probe generally is a polynucleotide that binds to the target nucleic acid molecule through complementary base pairing. It will be understood that a nucleic acid probe can specifically bind a target sequence that has less than complete complementarity with the probe sequence, and that the specificity of binding will depend, in part, upon the stringency of the hybridization conditions. A nucleic acid probes can be labeled as with a radionuclide, a chromophore, a lumiphore, a chromogen, a fluorescent protein, or a small molecule such as biotin, which itself can be bound, for example, by a streptavidin complex, thus providing a means to isolate the probe, including a target nucleic acid molecule specifically bound by the probe. By assaying for the presence or absence of the probe, one can detect the presence or absence of the target sequence or sub-sequence. The term "labeled nucleic acid probe" refers to a nucleic acid probe that is bound, either directly or through a linker molecule, and covalently or through a stable non-covalent bond such as an ionic, van der Waals or hydrogen bond, to a label such that the presence of the probe can be identified by detecting the presence of the label bound to the probe.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

The term "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "antibody" refers to a polypeptide substantially encoded by an immunoglobulin gene or immunoglobulin genes, or antigen-binding fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist as intact immunoglobulins and as well characterized antigen-binding fragments of an antibody, which can be produced by digestion with a peptidase or can using recombinant DNA methods. Such antigen-binding fragments of an antibody include, for example, Fv, Fab' and F(ab)'$_2$ fragments. The term "antibody," as used herein, includes antibody fragments either produced by the modification of whole antibodies or those synthesized de novo using recombinant DNA methodologies. As such, the present invention also provides an antibody or antigen-binding fragment thereof that specifically binds a chimeric phosphorylation indicator of the invention. Preferably, an antibody of the invention does not specifically bind the individual components that comprise the chimeric indicator, except when the components are part of the chimeric phosphorylation indicator. The term "immunoassay" refers to an assay that utilizes an antibody to specifically bind an analyte. An immunoassay is characterized by the use of specific binding properties of a particular antibody to isolate, target, and/or quantify the analyte.

The term "identical," when used in reference to two or more polynucleotide sequences or two or more polypeptide sequences, refers to the residues in the sequences that are the same when aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any well known algorithm (see, for example, Meyers and Miller, *Comp. Appl. Biol. Sci.* 4:11–17, 1988; Smith and Waterman, *Adv. Appl. Math.* 2:482, 1981; Needleman and Wunsch, *J. Mol. Biol.* 48:443, 1970; Pearson and Lipman, *Proc. Natl. Acad. Sci., USA* 85:2444 (1988); Higgins and Sharp, *Gene* 73:237–244, 1988; Higgins and Sharp, *CABIOS* 5:151–153; 1989; Corpet et al., *Nucl. Acids Res.* 16:10881–10890, 1988; Huang, et al., *Comp. Appl. Biol. Sci.* 8:155–165, 1992; Pearson et al., *Meth. Mol. Biol.,* 24:307–331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a non-oligomerizing fluorescent protein also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K);
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point (Tm) for the specific sequence at a defined ionic strength and pH. The Tm is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset of codons from among the set of codons encoding an amino acid that are most frequently used in proteins expressed in mammalian cells as chosen from the following list: Gly (GGC, GGG); Glu (GAG); Asp (GAC); Val (GUG, GUC); Ala (GCC, GCU); Ser (AGC, UCC); Lys (AAG); Asn (AAC); Met (AUG); Ile (AUC); Thr (ACC); Trp (UGG); Cys (UGC); Tyr (UAU, UAC); Leu (CUG); Phe (UUC); Arg (CGC, AGG, AGA); Gln (CAG); His (CAC); and Pro (CCC).

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize $R_O$, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild type Aequorea GFP and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, which fluoresce when exposed to ultraviolet light, are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of Aequorea GFP can be derived from the naturally occurring GFP by engineering mutations such as amino acid substitutions into the reference GFP protein. For example ECFP is a spectral variant of GFP that contains substitutions with respect to GFP (compare SEQ ID NOS: 2 and 6).

Many cnidarians use green fluorescent proteins as energy transfer acceptors in bioluminescence. The term "green fluorescent protein" is used broadly herein to refer to a protein that fluoresces green light, for example, Aequorea GFP (SEQ ID NO:2). GFPs have been isolated from the Pacific Northwest jellyfish, Aequorea victoria, the sea pansy, Renilla reniformis, and Phialidium gregarium (Ward et al., Photochem. Photobiol. 35:803–808, 1982; Levine et al., Comp. Biochem. Physiol. 72B:77–85, 1982, each of which is incorporated herein by reference). Similarly, reference is made herein to "red fluorescent proteins", which fluoresce red, "cyan fluorescent proteins," which fluoresce cyan, and the like. RFPs, for example, have been isolated from the coral, Discosoma (Matz et al., supra, 1999).

A variety of Aequorea GFP-related fluorescent proteins having useful excitation and emission spectra have been engineered by modifying the amino acid sequence of a naturally occurring GFP from A. victoria (see Prasher et al., Gene 111:229–233, 1992; Heim et al., Proc. Natl. Acad. Sci., USA 91:12501–12504, 1994; U.S. Ser. No. 08/337,915, filed Nov. 10, 1994; International application PCT/US95/14692, each of which is incorporated herein by reference). As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 85% sequence identity with the reference fluorescent protein, and particularly has a contiguous sequence of at least about 200 amino acids that shares at least about 95% sequence identity with the reference fluorescent protein. Thus, reference is made herein to an "Aequorea-related fluorescent protein" or to a "GFP-related fluorescent protein," which is exemplified by the various spectral variants and GFP mutants that have amino acid sequences that are substantially identical to *A. victoria* GFP (SEQ ID NO:2), to a "*Discosoma*-related fluorescent protein" or a "DsRed-related fluorescent related protein," which is exemplified by the various mutants that have amino acid sequences substantially identical to that of DsRed (SEQ ID NO:12), and the like, for example, a *Renilla*-related fluorescent protein or a *Phialidium*-related fluorescent protein.

The term "mutant" or "variant" also is used herein in reference to a fluorescent protein to refer to a fluorescent protein that contains a mutation with respect to a corresponding wild type fluorescent protein. In addition, reference is made herein the a "spectral variant" or "spectral mutant" of a fluorescent protein to indicate a mutant fluorescent protein that has a different fluorescence characteristic with respect to the corresponding wild type fluorescent protein. For example, CFP, YFP, ECFP (SEQ ID NO:6), EYFP-V68L/Q69K (SEQ ID NO:10), and the like are GFP spectral variants.

*Aequorea* GFP-related fluorescent proteins include, for example, wild type (native) *Aequorea victoria* GFP (Prasher et al., supra, 1992; see, also, SEQ ID NO:2), allelic variants of SEQ ID NO:2, for example, a variant having a Q80R substitution (Chalfie et al., *Science* 263:802–805, 1994, which is incorporated herein by reference); and spectral variants of GFP such as CFP, YFP, and enhanced and otherwise modified forms thereof (U.S. Pat. Nos. 6,150,176; 6,124,128; 6,077,707; 6,066,476; 5,998,204; and 5,777,079, each of which is incorporated herein by reference), including GFP-related fluorescent proteins having one or more folding mutations, and fragments of the proteins that are fluorescent, for example, an *A. victoria* GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

Folding mutations in *Aequorea* GFP-related fluorescent proteins improve the ability of the fluorescent proteins to fold at higher temperatures, and to be more fluorescent when expressed in mammalian cells, but have little or no effect on the peak wavelengths of excitation and emission. If desired, these mutations can be combined with additional mutations that influence the spectral properties of GFP to produce proteins with altered spectral and folding properties, and, particularly, with mutations that reduce or eliminate the propensity of the fluorescent proteins to oligomerize. Folding mutations, with respect to SEQ ID NO:2, include the substitutions F64L, V68L, S72A, T44A, F99S, Y145F, N146I, M153T, M153A, V163A, I167T, S175G, S205T, and N212K.

The term "loop domain" refers to an amino acid sequence of an *Aequorea*-related fluorescent protein that connects the amino acids involved in the secondary structure of the eleven strands of the β-barrel or the central α-helix (residues 56–72). The term "fluorescent protein moiety," when used in reference to a fluorescent protein, refers to a portion of the amino acid sequence of the fluorescent protein that, when the amino acid sequence of the fluorescent protein substrate is optimally aligned with the amino acid sequence of a naturally occurring fluorescent protein, lies between the amino terminal and carboxy terminal amino acids, inclusive, of the amino acid sequence of the naturally occurring fluorescent protein, and comprises a chromophore, which fluoresces upon exposure to an appropriate wavelength of light.

Fluorescent proteins fused to target proteins can be prepared using recombinant DNA methods, and used as markers to identify the location and amount of the target protein produced. Accordingly, the present invention provides fusion proteins comprising a non-oligomerizing fluorescent protein moiety and a polypeptide of interest. The polypeptide of interest can be of any length, for example, about 15 amino acid residues, about 50 residues, about 150 residues, or up to about 1000 amino acid residues or more, provided that the fluorescent protein component of the fusion protein can fluoresce or can be induced to fluoresce when exposed to electromagnetic radiation of the appropriate wavelength. The polypeptide of interest can be, for example, a peptide tag such as a polyhistidine sequence, a c-myc epitope, a FLAG epitope, and the like; can be an enzyme, which can be used to effect a function in a cell expressing a fusion protein comprising the enzyme or to identify a cell containing the fusion protein; can be a protein to be examined for an ability to interact with one or more other proteins in a cell, or any other protein as disclosed herein or otherwise desired.

Fluorescent characteristics of *Aequorea* GFP-related fluorescent proteins depend, in part, on the electronic environment of the chromophore. In general, amino acids that are within about 0.5 nm of the chromophore influence the electronic environment of the chromophore. Therefore, substitution of such amino acids can produce fluorescent proteins with altered fluorescent characteristics. In the excited state, electron density tends to shift from the phenolate towards the carbonyl end of the chromophore. Therefore, placement of increasing positive charge near the carbonyl end of the chromophore tends to decrease the energy of the excited state and cause a red-shift in the absorbance and emission wavelength maximum of the protein. Decreasing a positive charge near the carbonyl end of the chromophore tends to have the opposite effect, causing a blue-shift in the protein's wavelengths. Similarly, mutations have been introduced into DsRed to produce mutants having altered fluorescence characteristics (see Example 2).

Amino acids with charged (ionized D, E, K, and R), dipolar (H, N, Q, S, T, and uncharged D, E and K), and polarizable side groups (e.g., C, F, H, M, W and Y) are useful for altering the ability of fluorescent proteins to oligomerize, especially when they substitute an amino acid with an uncharged, nonpolar or non-polarizable side chain (see Examples 1 and 3). As disclosed herein, substitution of hydrophobic residues that were predicted to be involved in self-association of GFP with positively-charged residues reduced or eliminated dimerization. However, other non-conservative amino acid substitutions also can be introduced similarly or at neighboring positions in the interacting regions of the proteins, thus disrupting the localized structure of the protein, provided the substitutions do not undesirably affect the fluorescent properties of the proteins.

The present invention also relates to polynucleotide encoding a chimeric phosphorylation indicator of the invention. In one embodiment, the polynucleotide encodes a chimeric phosphorylation indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor. In another embodiment, the polynucleotide encodes a chimeric phosphorylation indicator containing a phosphorylatable polypeptide and a fluorescent protein, wherein the phosphorylatable polypeptide includes an N-terminal portion and a C-terminal portion, and the fluorescent protein is operatively inserted between the N-terminal portion and C-terminal portion of the phosphorylatable polypeptide. In still another embodiment, the polynucleotide encodes a chimeric phosphorylation indicator containing a phosphoaminoacid binding domain operatively linked to a phosphorylatable polypeptide and a fluorescent protein, wherein the fluorescent protein includes an N-terminal portion and a C-terminal portion, and wherein the phosphorylatable polypeptide and operatively linked phosphoaminoacid binding domain is operatively inserted between the N-terminal portion and C-terminal portion of the fluorescent protein.

Also provided is a vector containing a polynucleotide of the invention, including an expression vector, as well as host cells that contain a polynucleotide of the invention or a vector containing such a polynucleotide. In one embodiment, a polynucleotide of the invention is operatively linked to an expression control sequence, for example, a transcription regulatory element, a translation regulatory element, or a combination thereof. In another embodiment, the polynucleotide is operatively linked to a nucleotide sequence encoding a membrane translocating domain or a cell compartmentalization domain.

A vector generally contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol., Vol.* 185, Goeddel, ed. (Academic Press, Inc., 1990); Jolly, *Canc. Gene Ther.* 1:51–64, 1994; Flotte, *J. Bioenerg. Biomemb.* 25:37–42, 1993; Kirshenbaum et al., *J. Clin. Invest.* 92:381–387, 1993; each of which is incorporated herein by reference).

A vector for containing a polynucleotide encoding a chimeric phosphorylation indicator can be a cloning vector or an expression vector, and can be a plasmid vector, viral vector, and the like. Generally, the vector contains a selectable marker independent of that encoded by a polynucleotide of the invention, and further can contain transcription or translation regulatory elements, including a promoter sequence, which can provide tissue specific expression of a polynucleotide operatively linked thereto, which can, but need not, be the polynucleotide encoding the chimeric phosphorylation indicator, thus providing a means to select a particular cell type from among a mixed population of cells containing the introduced vector and recombinant nucleic acid molecule contained therein.

Where the vector is a viral vector, it can be selected based on its ability to infect one or few specific cell types with relatively high efficiency. For example, the viral vector also can be derived from a virus that infects particular cells of an organism of interest, for example, vertebrate host cells such as mammalian host cells. Viral vectors have been developed for use in particular host systems, particularly mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980–990, 1992; Anderson et al., *Nature* 392:25–30 Suppl., 1998; Verma and Somia, *Nature* 389:239–242, 1997; Wilson, *New Engl. J. Med.* 334:1185–1187 (1996), each of which is incorporated herein by reference).

Recombinant production of a chimeric phosphorylation indicator involves expressing a polypeptide encoded by a polynucleotide. The sequence of the polynucleotide can be confirmed using routine methods, including, for example, PCR methods (see, for example, U.S. Pat. No. 4,683,195; Mullis et al., *Cold Spring Harbor Symp. Quant. Biol.* 51:263, 1987; Erlich, ed., "PCR Technology" (Stockton Press, NY, 1989)). The construction of expression vectors and the expression of a polynucleotide in transfected cells involves the use of molecular cloning techniques also well known in the art (see Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements). Expression vectors contain expression control sequences operatively linked to a polynucleotide sequence of interest, for example, that encoding a non-oligomerizing fluorescent protein, as indicated above. The expression vector can be adapted for function in prokaryotes or eukaryotes by inclusion of appropriate promoters, replication sequences, markers, and the like. An expression vector can be transfected into a recombinant host cell for expression of a chimeric phosphorylation indicator, and host cells can be selected, for example, for high levels of expression in order to obtain a large amount of isolated protein. A host cell can be maintained in cell culture, or can be a cell in vivo in an organism.

An expressed chimeric phosphorylation indicator can be operatively linked to a polypeptide of interest, for example, a peptide tag, which can be used to facilitate isolation of the indicator. For example, a polyhistidine tag containing, for example, six histidine residues, can be incorporated at the N-terminus or C-terminus of the chimeric phosphorylation indicator, which then can be isolated in a single step using nickel-chelate chromatography (see Example 1). Additional peptide tags, including a c-myc peptide, a FLAG epitope, or any ligand (or cognate receptor), including any peptide epitope (or antibody, or antigen binding fragment thereof, that specifically binds the epitope are well known in the art and similarly can be used. (see, for example, Hopp et al., *Biotechnology* 6:1204, 1988; U.S. Pat. No. 5,011,912, each of which is incorporated herein by reference).

Kits also are provided to facilitate and, where desired, standardize the compositions of the invention and the uses thereof. A kit can contain one or more compositions of the invention, for example, one or a plurality of chimeric phosphorylation indicators, or one or a plurality of polynucleotides that encode the indicators. In addition, the kit can contain instructions for using the components of the kit, particularly the compositions of the invention that are contained in the kit.

Such kits can be particularly useful where they provide a plurality of different chimeric phosphorylation indicators because the artisan can conveniently select one or more indicators having the properties desired for a particular application. Similarly, a kit containing a plurality of polynucleotides encoding different chimeric phosphorylation indicators provides numerous advantages. For example, the polynucleotides can be engineered to contain convenient restriction endonuclease or recombinase recognition sites, thus facilitating operative linkage of the polynucleotide to a regulatory element or to a polynucleotide encoding a phosphorylatable domain or PAABD of interest.

The present invention further relates to a method for detecting a kinase or phosphatase in a sample. In one embodiment, a method of the invention is performed, for example, contacting the sample with a chimeric phosphorylatable indicator, which contains, in operative linkage, a donor molecule, a phosphorylatable domain, a phosphoaminoacid binding domain, and an acceptor molecule, wherein the phosphoaminoacid binding domain specifically binds to a phosphoaminoacid when present in the phosphorylatable domain, the donor molecule and the acceptor molecule exhibit a detectable resonance energy transfer when the donor is excited, and the phosphorylatable domain and phosphoaminoacid binding domain do not substantially emit light to excite the acceptor; exciting the donor molecule; and determining a fluorescence or luminescence property in the sample, wherein the presence of a kinase or phosphatase in the sample results in a change in the degree of FRET or LRET, thereby detecting the kinase or phosphatase in the sample. The change in the degree of FRET or LRET can be an increased amount of FRET or LRET, or can be a decreased amount of FRET or LRET, and the change can be indicative of the presence of a kinase in the sample, or, where the phosphorylatable domain is phosphorylated prior to contacting the sample with a chimeric phosphorylatable indicator, can be indicative of a phosphatase in the sample.

Fluorescence in a sample generally is measured using a fluorimeter, wherein excitation radiation from an excitation source having a first wavelength, passes through excitation optics, which cause the excitation radiation to excite the sample. In response, a non-oligomerizing fluorescent protein in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves a microtiter plate holding a plurality of samples in order to position different wells to be exposed. The multi-axis translation stage, temperature controller, auto-focusing feature, and electronics associated with imaging and data collection can be managed by an appropriately programmed digital computer, which also can transform the data collected during the assay into another format for presentation. This process can be miniaturized and automated to enable screening many thousands of compounds in a high throughput format. These and other methods of performing assays on fluorescent materials are well known in the art (see, for example, Lakowicz, "Principles of Fluorescence Spectroscopy" (Plenum Press 1983); Herman, "Resonance energy transfer microscopy" In "Fluorescence Microscopy of Living Cells in Culture" Part B, *Meth. Cell Biol.* 30:219–243 (ed. Taylor and Wang; Academic Press 1989); Turro, "Modern Molecular Photochemistry" (Benjamin/Cummings Publ. Co., Inc. 1978), pp. 296–361, each of which is incorporated herein by reference).

In another embodiment, a method for detecting a kinase or phosphatase in a sample is performed by contacting the sample with a chimeric phosphorylatable indicator containing a phosphorylatable polypeptide and a fluorescent protein, determining a fluorescence property in the sample, wherein the presence of kinase or phosphatase activity in the sample results in a change in the fluorescence property as compared to the fluorescent property in the absence of a kinase or phosphatase activity, thereby detecting the kinase or phosphatase in the sample. The chimeric phosphorylation indicator can containing a phosphorylatable polypeptide that includes an N-terminal portion and a C-terminal portion, such that the fluorescent protein is operatively inserted between the N-terminal portion and C-terminal portion of the phosphorylatable polypeptide; or the chimeric phosphorylation indicator can contain a phosphoaminoacid binding domain operatively linked to a phosphorylatable polypeptide, which is operatively inserted between an N-terminal portion and a C-terminal portion of the fluorescent protein.

The sample to be examined for kinase activity can be any sample, including, for example, a sample containing a synthetic product to be examined for kinase or phosphatase activity. In one embodiment, the sample is a biological sample, which can be cell, tissue or organ sample, or an extract of such a sample. In another embodiment, the method is performed on an intact cell, which can be in cell culture or can be in a tissue sample. For such a method, the chimeric phosphorylatable indicator can contain a targeting sequence such as a cell compartmentalization domain that can target the chimeric phosphorylatable indicator to cytosol, endoplasmic reticulum, mitochondrial matrix, chloroplast lumen, medial trans-*Golgi cisternae*, a lumen of a lysosome, or a lumen of an endosome. A membrane translocating domain can be a particularly useful cell compartmentalization domain is a membrane translocating domain, which can facilitate translocation of the chimeric phosphorylation indicator into an intact cell.

The phosphorylatable polypeptide in a chimeric phosphorylation indicator comprising a fluorescent protein and a phosphorylatable polypeptide can be unphosphorylated or phosphorylated at an amino acid position specific for a kinase or a phosphatase, depending on whether the method is for detecting a kinase or phosphatase. A method of the invention also can be used to detect an absence of kinase or phosphatase activity in the sample is due to the presence of a kinase inhibitor or phosphatase inhibitor. As such, the method is useful for identifying a kinase inhibitor or a phosphatase inhibitor.

The following examples are intended to illustrate, but not limit, the present invention.

EXAMPLE 1

Preparation and Characterization of a Chimeric Reporter Protein for a Serine/Threonine Protein Kinase This example provides a method for preparing a chimeric protein kinase A (PKA; cAMP-dependent protein kinase) reporter protein, and demonstrates that such a chimeric reporter molecule can detect serine/threonine kinase activity.

Plasmid Construction.

The PKA chimeric reporter protein was constructed by fusing the enhanced cyan fluorescent protein (1–227; ECFP; SEQ ID NO:6; K26R/F64L/S65T/Y66W/N146I/M153T/V163A/N164H), a truncated version of 14-3-3τ, a modified kemptide and citrine, which is an improved yellow fluorescence protein having a sequence as set forth in SEQ ID NO:10, except containing a Q69M mutation. 14-3-3τ (1–232) was amplified using the cDNA of 14-3-3τ (see GenBank Accession No. D87662, which is incorporated herein by reference) in pcDNA3 vector as the template.

For PCR, the forward primer had the sequence 5'-GGGCATGCATATGGAGAAGACTGAGCTGATCCA-G-3' (SEQ ID NO:26), and incorporates a Sph I site. The reverse primer had the sequence 5'-CGCGGAGCTCGCTGCCGCCGGTGCCGCCCAG-GCTGGCGCGACGGAG GCTGCCGCCGGTGCC- GCCTGCAGAGTCTGATGTCCAAAGTGTTAGG-3' (SEQ ID NO:27), which introduces a short linker peptide (AGGTGGS; SEQ ID NO:19), the kemptide sequence (LRRASLG; SEQ ID NO:32), a second short linker peptide (GTGGSEL; SEQ ID NO:21) and a Sac I site.

PCR was performed using 50 ng of template, 300 nM of each primer, 500 nM of each dNTP, 2.5 Unit of Taq polymerase (Gibco) in 1×PCR reaction buffer (Boehringer Mannheim) with nanopure water (50 μl total volume). PCR was performed as follows: 95° C., 5 min; 2 cycles of (95° C., 1 min; 40° C., 1 min; 72° C., 2.5 min); 5 cycles of (95° C., 1 min; 43° C., 1 min; 72° C., 2.5 min); 5 cycles of (95° C., 1 min; 45° C., 1 min; 72° C., 2.5 min); 15 cycles of (95° C., 1 min; 52° C.m 1 min; 72° C., 2.5 min; 72° C., 7 min), then hold at 25° C.

The amplification product was purified using the Qiagen gel purification kit, then digested with Sph I and Sac I overnight. The digested mixture was purified using Qiagen PCR purification kit, and the purified fragment was ligated into Sph I/Sac I-digested pRSET$_B$ (Invitrogen) containing the cDNA sequence for ECFP and citrine (from Yellow cameleon 3.3). The construct was within the Bam HI/Eco RI sites of pRSET$_B$, and is behind a polyhistidine tag for bacterial expression. The resulting plasmid was amplified, sequenced and mutagenized using the QUICKCHANGE™ site-directed mutagenesis kit (Stratagene) to introduce one amino acid change in the kemptide sequence, generating the plasmid C4kY2.1-pRSET$_B$.

```
Primers for mutagenesis had the following
sequence:
                                    (SEQ ID NO:28)
5'-CGTCGCGCCAGCCTGCCAGGCACCGGCGGCAGC-3', and (SEQ ID NO:29)
5'-GCTGCCGCCGGTGGCTGGCAGGCTGGCGCGACG-3'.

The S475A mutant was generated similarly using the
following primers:
                                    (SEQ ID NO:30)
GCCTCCGTCGCGCCGCACTGCCAGGCACCGGC; and (SEQ ID NO:31)
GCCGGTGCCTGGCAGTGCGGCGCGACGGAGGC.
```

For mammalian expression, both C4kY2.1 and C4kY2.1 (S475A) were cloned into the vector pcDNA3 behind a Kozak sequence for mammalian expression.

Protein Expression, Phosphorylation and In Vitro Spectroscopy.

C4kY2.1-pRSET$_B$ and C4kY2.1 (S475A)-pRSET$_B$ each were transformed into E. coli strain BL21(DE3). A single colony was picked and grown in 100 to 500 ml LB medium containing 0.1 mg/ml ampicillin at 37° C. to an optical density of 0.4–0.8 at 600 nm, then induced with 0.1 mg/ml isopropyl thiogalactoside (IPTG) at 25° C. for 12 to 24 hr. Cells were harvested by centrifugation, then the bacterial pellet was suspended in 4 to 10 ml B-PER™ II Bacterial Extraction Reagent (Pierce) and lysed by gentle shaking at 25° C. for 15 min in the presence of protease inhibitors (COMPLETE™ EDTA-free Protease Inhibitor tablet (Roche), 1 mM phenylmethylsulfonyl fluoride). The lysate was clarified by centrifugation at 12,000 g for 30 min at 4° C.

Binding of the His$_6$ tag to Ni-NTA agarose (Qiagen) was carried out in a batch mode. The supernatant was filtered through a 0.22 μM syringe filter, then transferred to a new tube, to which 0.3 to 1 ml of the 50% (v/v) Ni-NTA slurry was added. The suspension was mixed gently on a rotary shaker at 4° C. for 1 hr. The lysate-Ni-NTA mixture was loaded into a column, which was washed with 10 volumes of TNS300 buffer (Tris-HCl, pH 7.4, 300 mM NaCl) and 10 volumes of TNS300 containing 10 mM imidazole. The chimeric protein was eluted with 1 to 3 ml of elution buffer (100 mM imidazole in TNS300) and dialyzed in TNS300 buffer at 4° C. for 12 to 24 hr. When necessary, the protein was concentrated using a YM-30 MICROCON™ or CENTRICON™ concentrator (Fisher).

Chimeric proteins were phosphorylated with the catalytic subunit of PKA (New England Biolabs; 2.5U/μl) in PKA kinase reaction buffer (50 mM Tris-HCl, pH 7.5, 10 mM MgCl$_2$, 1 mg/ml BSA) in the presence of an optional amount of adenosine triphosphate, ATP (200 μM to 1 mM) at 25° C. Fluorescence was monitored using an excitation wavelength of 434 nm before and after adding ATP to the rest of the components. Experiments were performed in a Perkin-Elmer Spectrofluorometer LS50B. Emission spectra (excitation 380 nm, emission 430 to 650 nm) were collected and 536/476 emission ratios calculated at each time point.

For in vitro kinase assay, different constructs were incubated with 7.5 unit of catalytic subunit of PKA and 6.5 nM (1.2 μCi) γ-$^{32}$P)-ATP (6000 Ci/mmol, New England Nuclear) in PKA kinase reaction buffer, in a total volume of 30 μl at 25° C. for 30 min to 12 hr. Ten μl of the reaction mixture was spotted onto a phosphocellulose disk, immersed in 0.5% H$_3$PO$_4$ and washed with the PKA kinase reaction buffer three times, for 10 min each. Transfer of $^{32}$P was measured by standard scintillation counting.

For testing the specificity of the reporter, fluorescence change and transfer of $^{32}$P upon incubation with CaMKII (New England Biolabs) and PKCβII were followed similarly. The reaction conditions for CaMKII was 5U/μl CaMKII, 1 mM ATP or 6.5 nM (1.2 μCi) (γ-$^{32}$P)ATP (6000 Ci/mmol, NEN), 2 mM CaCl$_2$, 2.4 μM calmodulin in CaMKII buffer (20 mM Tris-HCl, pH 7.5, 10 mM MgCl$_2$, 0.5 mM dithiothreitol and 0.1 mM Na$_2$EDTA) at 25° C. for 30 min to 12 hr. The reaction conditions for PKCβII was 3U/μl PKCβII, 1 mM ATP or 6.5 nM (1.2 μCi) (γ-$^{32}$P)-ATP (6000 Ci/mmol), 5 mM CaCl$_2$, 140 μM phosphatidylserine and 3.8 μM diacylglycerol in buffer (20 mM Tris-HCl, pH 7.5, 10 mM MgCl$_2$) at 25° C. for 30 min to 12 hr.

For testing phosphatases, the PKA-phosphorylated chimeric reporter protein was concentrated using a YM-30 MICROCON™ concentrator and an equal volume of TNS300 buffer was added. The protein was then purified by Ni-NTA as described above. The purified protein was dephosphorylated with 2.5 U protein phosphatase 1 (PP1; New England Biolabs) in the presence of 1 mM MnCl$_2$ in PP1 buffer (50 mM Tris-HCl, pH 7.0, 0.1 mM Na$_2$EDTA, 5 mM DTT, 0.01% Brij35) at 25° C. for 30 min to 3 hr.

Cell Culture.

HeLa cells or COS-7 cells were plated onto sterilized glass coverslips in 2 cm dishes or in 10 cm plates and grown to 50–90% confluency at 37° C. in low-glucose DMEM medium. Cells were transfected with the FuGENE-6 transfection reagent (Roche). Briefly, cells on 24-mm glass coverslips in a 2 cm dish were transfected with 0.5 μg DNA (purified using the Midiprep Kit from Qiagen), 100 μl of OptiMEM1 medium and 3 μl of FuGENE-6. After a 30 min incubation at room temperature, the mixture was added to the cells.

For imaging analysis, cells were incubated for 24–72 hr at 37° C. in fetal bovine serum in low glucose DMEM, then washed twice with HBSS buffer (20 mM Hepes, pH 7.4, 2 g/l D-glucose), maintained in buffer in the dark at room temperature, with addition of forskolin (FsK; Calbiochem) and $N^6$, 2'-O-dibutyryl cyclic adenosine 3',5' monophosphate (dbcAMP; Calbiochem). FsK was dissolved in DMSO to be used as a 50 mM stock solution. To add a DMSO solution, 500 µl of HBSS buffer was taken from the imaging dish and mixed with the DMSO solution, then added back to the imaging dish. For inhibition studies of PKA activity, cells were preincubated in DMEM medium containing 10 µM H-89 for approximately 2 hr.

Imaging Studies

Cells were imaged on a Zeiss Axiovert microscope with a cooled CCD camera (Photometrics; Tucson Ariz.), controlled by METAFLUOR 2.75™ software (Universal Imaging; West Chester Pa.). Dual-emission ratio imaging used a 440DF30 excitation filter, a 455DRLP dichroic mirror and two emission filters (480DF30 for ECFP, 535DF25 for citrine) altered by a filter changer (Lambda 10-2, Sutter Instruments, San Rafael, Calif.). Fluorescence images were background-corrected. Exposure time was 1000 ms and images were taken every 15 sec.

Results

The protein kinase, PKA, which is involved in cell signaling, was used to exemplify a ratiometric indicator for serine/threonine phosphorylation. cAMP is one if the main second messengers and plays an important role as a signal transducer in many cellular activities, the signal being transmitted by activation of PKA. PKA regulates specific gene expression by phosphorylating specific nuclear proteins at serine/threonine residues within consensus sequences. The 14-3-3 family of proteins mediates signal transduction by binding to phosphoserine-containing proteins and, therefore, can contain a consensus sequence that could encompass consensus site for PKA. Accordingly, fusion proteins were constructed in which a GFP FRET pair were linked by a 14-3-3 protein and a substrate peptide. Upon phosphorylation, binding between 14-3-3 and the substrate can bring two GFPs into proximity such that FRET is enhanced as the readout for phosphorylation. For the GFP FRET pair, ECFP and citrine, which is an improved yellow fluorescence protein with a better stability to acid conditions, were selected. The C-terminal tail of 14-3-3 was omitted, and replaced with a flexible linker AGGTGGS (SEQ ID NO:19). Another flexible linker GGTGGSEL (SEQ ID NO:21) was inserted between the substrate peptide and citrine.

A number of chimeras containing different substrate sequences, including the kemptide (LRRASLG; SEQ ID NO:32), a modified kemptide (LRRASLP; SEQ ID NO:20) and a peptide sequence derived from Raf-259 (AQRSTSTPN; SEQ ID NO:33), were generated. The C4kY2.1 reporter (FIG. 6B) gave the best response to the activation of PKA. C4kY1.1 containing the kemptide sequence also was responsive to the activation of PKA. While the 14-3-3 recognized a consensus sequence RSX-SXP (SEQ ID NO:34), it was rationalized that mutagenizing the glycine at the +2 position with respect to the serine, to a proline, could increase the binding affinity. As such, the C4kY2.1 chimeric reporter protein was constructed containing a modified kemptide sequence.

In Vitro Characterization of a Chimeric Reporter Protein

The chimeric reporter protein C4kY2.1 was efficiently phosphorylated by the catalytic subunit of PKA, while the mutant C4kY2.1 (S475A) protein was not phosphorylated in the in vitro phosphorylation assay. This result indicates that phosphorylation occurs at the designated serine in the modified kemptide sequence (LRRA$\underline{S}^{475}$LP; SEQ ID NO:20) containing the consensus PKA phosphorylation site (RRXS; SEQ ID NO:35).

The effect of a structural alteration due to phosphorylation on the efficiency of FRET also was examined. Excitation of the fluorophore in the ECFP at 434 nm results in fluorescence emission at 526 nm from the citrine due to FRET between the two fluorophores. When the C4kY2.1 chimeric reporter protein was phosphorylated, FRET was increased and the ratio of the emission at 526 nm and 476 nm increased from a value of 1.09 to 1.42 in a time-dependent manner. Negative controls, in which either PKA or ATP were omitted, demonstrated that FRET change is dependent on the PKA phosphorylation. The mutant C4kY2.1 (S475A), in which the designated serine was mutated to an alanine did not give any change of FRET upon incubation with PKA catalytic subunit and 1 mM ATP. This result demonstrates that the FRET change is due to a conformational change, for example, due to binding between the phosphorylated peptide and 14-3-3, which is induced by the PKA phosphorylation at the serine 475.

Following treatment of the C4kY2.1 chimera with 10 µg of trypsin for 40 min (Miyawaki and Tsien, Meth. Enzymol. 37:472–500, 2000, which is incorporated herein by reference), FRET efficiencies of phosphorylated and non-phosphorylated C4kY2.1 were calculated to be 20 and 30%, respectively. Furthermore, the PKA/ATP-dependent FRET change was reversible upon treatment with protein phosphatase 1 (PP1), which is specific for phosphorylated serine/threonine. When the purified PKA-phosphorylated chimera was incubated with PP1, FRET was decreased and the emission ratio of 526 nm and 476 nm decreased from a value of 1.39 to 1.14 in a time-dependent manner.

The specificity of the chimeric PKA reporter protein C4kY2.1 was examined by applying CaMKII and PKCβII to the chimera in vitro. These two kinases have the consensus sequences RXXS/T (SEQ ID NO:36) and K/RXXS/T (SEQ ID NO:37), respectively, which overlap with the kemptide sequence. The chimera was poorly phosphorylated by both kinases, and incubation of the chimera with the either kinase did not result in a significant FRET change. These results demonstrate that the C4kY2.1 chimera is specific to PKA phosphorylation in vitro.

Expression and Behavior of PKA Reporter in Mammalian Cells.

When the chimeric PKA reporter C4kY2.1 was transfected into HeLa cells, the fluorescence was uniformly distributed in the cytosolic compartment, but was excluded from the nucleus, as expected for such a chimeric protein that lacked targeting signals. A similar expression pattern also was observed in COS-7 cells. To elevate the activities of PKA, transfected cells were treated with cAMP-elevating agents. Exposure of the cells to 50 µM FsK and 1 mM dibutyryl cAMP increased the 535 nm/480 nm ratio in a time-dependent manner. Typically the ratio reached a plateau at 5 min after stimulation. When C4kY2.1 (S475A) transfected cells were treated in the same condition, no change in the 535 nm/480 nm ratio was observed. This result is consistent with the intramolecular binding between 14-3-3 and the peptide phosphorylated by PKA at the serine475 being responsible for the FRET change observed.

Either FsK or dbcAMP, alone, induced the FRET change. In general, the change in the emission ratio 535 nm/480 nm was from 25% to 34%. In addition, the change and kinetics were dependent on the fluorescence intensity of the trans fected cells; i.e., the brighter the cell, the bigger the FRET change and the more slowly the plateau was reached. Administration of 1 mM dbcAMP, alone, slowly increased the 535 nm/480 nm ratio, while pretreatment with 10 μM H-89, a PKA inhibitor, for 2 hr slowed down the process even more, but did not completely inhibited it. The change in the emission ratio 535 nm/480 nm in the cells pretreated with H-89 was 46%, suggesting that the pretreatment with the PKA inhibitor reduced the basal level of PKA phosphorylation inside cells prior to the stimulation, giving rise to a greater FRET change. A similar increase in the 535 nm/480 nm ratio was observed in COS-7 cells treated with FsK and with dbcAMP, although the change was smaller (about 5%) and a higher starting ratio was observed.

expression of the EGFR reporter. The structure of the chimeric EGFR reporter protein is illustrated in FIG. 7A.

For mammalian expression, the Eopt-pRSETB plasmid was cloned into the vector pCDNA3 using the Bam HI and Eco RI restriction sites. Constructs prepared in this way retained their N-terminal His$_6$ tags. The mammalian expression plasmid was named "Eopt-pCDNA3".

Preparation of the Chimeric Gene Encoding the Chimeric Src Reporter Protein

The SH2 domain from v-Src was amplified by PCR using the following primers:

```
SrcSH2.Fwd-(5'-GCCGCTCGCATGCATTGGTATTTTGGGAAGATCAC-3';); and SEQ ID NO:40

SrcSH2.Rev-(5'-CACCATGAGCTCAAATTCACCGTAGATCTCAGAACCCT           SEQ ID NO:41

CACCAGAACCCGGCTTCCCAGATCCAGATGTAGACCCACAGACGTTAG

TCAGGCG-3';).
```

EXAMPLE 2

Preparation and Characterization of Chimeric Reporter Proteins for Detecting Tyrosine Kinase Activity This example provides methods for preparing a chimeric src reporter protein and a chimeric EGFR reporter protein, and demonstrates that such chimeric reporter proteins can detect tyrosine kinase activity.

Preparation of the Chimeric Gene Encoding the Chimeric EGFR Reporter Protein

The SH2 domain from mouse p52 Shc (see Lanning and Lafuse, *Immunogenetics* 49:498–504, 1999; GenBank Accession No. AF054823, each of which is incorporated herein by reference) was amplified by PCR using the following primers:

The PCR reaction was assembled as 67 μl of water, 10 μl of 10X Taq buffer (Promega), 16 μl of 25 mM MgCl$_2$, 2 μl of a 25 mM stock of dNTPs, 1.5 μl of 100 μM SrcSH2.Fwd primer, 1.5 μl of 100 μM SrcSH2.Rev primer, 1 μl of 0.1 μg/μl v-Src template, and 1 μl of Taq polymerase (Promega). The following cycle was used: 94° C., 2 min; 2 cycles of (95° C., 2 min; 40° C., 2 min; 72° C., 2:30 min); 28 cycles of (95° C., 1 min; 52° C., 1 min; 72° C., 2:30 min); 72° C., 10 min; 25° C. hold.

The PCR product was digested with Sac I and Sph I and ligated into YC3.3 plasmid digested with the same enzymes. This construct, called "SC-pRSETB", was used for bacterial expression of the Src reporter. The structure of the chimeric Src reporter protein is illustrated in FIG. 7B.

For mammalian expression, the SC-pRSETB plasmid was cloned into the vector pCDNA3 using the Bam HI and Eco RI restriction sites. Constructs prepared in this way retained their N-terminal His$_6$ tags. The mammalian expression plasmid was named "SC-pCDNA3".

Preparation of the Chimeric EGFR Reporter Protein and Chimeric Src Reporter Protein from Bacterial Cells

```
EGFR.Fwd-(5'-GCCGCCCGCATGCATTGGTTCCACGGGAAGCTGAGCCGG-3';), and SEQ ID NO:38

EGFRoptsub.Rev-(5'-TACCATGAGCTCTGATTGCGGAGCCATGTTCATG           SEQ ID NO:39

TACTCAGCTTCCTCTTCAGGCTTCCCAGATCCAGAGTGAGACCCCACG

GGTTGCTCTAGGCACAG-3';).
```

The PCR reaction was assembled as: 67 μl of water, 10 μl of 10×Taq buffer (Promega), 16 μl of 25 mM MgCl$_2$, 2 μl of a 25 mM stock of dNTPs, 1.5 μl of 100 μM EGFR.Fwd primer, 1.5 μl of 100 μM EGFRoptsub.Rev primer, 1 μl of 0.1 μg/μl p52 Shc template, and 1 μl of Taq polymerase (Promega). The following cycle was used: 94° C., 2 min; 2 cycles of (95° C., 2 min; 40° C., 2 min; 72° C., 2:30 min); 28 cycles of (95° C., 1 min; 52° C., 1 min; 72° C., 2:30 min); 72° C., 10 min; 25° C. hold.

The PCR product was digested with Sac I and Sph I and ligated into similarly digested YC3.3 plasmid, which contained the genes for EYFP and ECFP behind an N-terminal His$_6$ tag, and is derived from the vector pRSETB. This construct, called "Eopt-pRSETB", was used for bacterial For bacterial expression, chemically-competent DH5α bacteria were transformed with the Eopt-pRSETB plasmid. The cells were plated on LB agar supplemented with ampicillin (50 μg/ml). A single bacterial colony was used to inoculate an overnight 1 ml culture of LB supplemented with ampicillin (50 μg/ml), then the 1 ml culture was used inoculate a 500 ml culture of LB supplemented with ampicillin (50 μg/ml). The cells were grown at 37° C. until OD$_{600}$ of about 0.4, then protein expression was induced with the addition of 500 μl of 1 M IPTG. The cells were incubated with shaking at 30° C. for 6 to 12 hr more, then harvested by centrifugation in GS-3 tubes at 4° C. for 10 min at 4000 rpm.

The cell pellet was resuspended in 10 ml of B-PERII Reagent (Pierce) and the mixture was incubated with gentle rocking at 25° C. for 10 min, then the cell debris was pelleted by centrifugation in SS-34 tubes at 4° C. for 15 min at 15,000 rpm. The supernatant was separated and combined with 1 ml of Ni-NTA agarose (Qiagen) and the suspension was incubated at 4° C. for 30 min with gentle rotation. The suspension then was transferred to a screening column and the beads were rinsed with 2×8 ml of 50 mM Tris pH 7.4/300 mM NaCl/10 mM imidazole. The chimeric protein was eluted with 5 ml of 50 mM Tris pH 7.4/300 mM NaCl/100 mM imidazole, then dialyzed overnight in 50 mM Tris pH 7.4/50 mM NaCl/10 mM $MgCl_2$ and stored in small aliquots at −20° C. The typical yield was 5 ml of 1–5 μM pure EGFR reporter protein.

The same procedure was used to prepare the chimeric Src reporter protein from bacterial cells.

Expression of the Chimeric EGFR Reporter Protein and Chimeric Src Reporter Protein in Mammalian Cells Eopt-pCDNA3 plasmid was amplified and purified using the endotoxin-free midiprep kit from Qiagen. For fluorescence measurements in living cells, mouse B82 cells, HeLa cells, or NIH3T3 cells in 2 cm dishes at 50–90% confluence were transfected with 1 μg of the Eopt-pCDNA3 plasmid using Fugene (Roche) according to standard protocols. The cells were incubated with the DNA for 10–24 h at 37° C. in 5% $CO_2$ and 10% calf (B82 cells and NIH3T3 cells) or fetal bovine serum (HeLa cells) in high glucose DMEM. The cells were then serum-starved in 0.5% calf serum (in high glucose DMEM) for 6 to 24 hr.

For biochemical analysis of the reporter expressed in mammalian cells, mouse B82 cells, HeLa cells, or NIH3T3 cells in 10 cm dishes at 50–90% confluence were transfected with 1 μg of the Eopt-pcDNA3 plasmid using EFFECTENE™ (Qiagen) according to standard protocols. The cells were incubated with the DNA for 10 to 24 hr at 37° C. in 5% $CO_2$ and 10% calf (B82 cells and NIH3T3 cells) or fetal bovine serum (HeLa cells) in high glucose DMEM. The cells were then serum-starved in 0.5% calf serum (in high glucose DMEM) for 6 to 24 hr.

Expression of the chimeric EGFR reporter protein was assessed by fluorescence in vitro. The assay was performed at room temperature in 50 mM Tris, pH 7.4, 50 mM NaCl, 10 mM $MgCl_2$, 100 μM ATP and EGFR enzyme (Sigma). CFP was excited at 400 nM, and CFP and YFP emissions were measured at 75 nM and 525 nm, respectively. A cutoff filter at 420 nm was used. The YFP:CFP ratio increased only when EGFR and ATP were included in the reaction mixture.

The identical procedure was used to express the chimeric Src reporter protein in mammalian cells, except that the in vitro response was performed using 50 mM Tris, pH 7.4, 50 mM NaCl, 10 mM $MgCl_2$, 100 μM ATP and c-Src enzyme (Upstate Biotechnology). CFP was excited at 432 nM, and CFP and YFP emissions were measured at 475 nm and 525 nm, respectively.

Fluorescence Measurements of the Chimeric EGFR and Src Reporter Proteins in Mammalian Cells Live-cell imaging was performed as described for the cameleon $Ca^{+2}$ indicators (Miyawaki et al., Nature 388:882–887, 1997, which is incorporated herein by reference). EGFR was stimulated in HeLa cells and in mouse L cells by addition of 50 ng/ml of EGF (Sigma). For measuring the effect of inhibitor on the EGFR reporter, 100 nM of AG1478 (Calbiochem) was incubated with the cells in HBSS (20 mM Hepes, pH 7.4, 2 g/l D-glucose) for 30 min at room temperature prior to application of EGF.

Addition of EGF to the transfected mouse L cells resulted in an immediate increase in the emission ratio, and reached a plateau at about a 27% emission ratio change by about 2 minutes. Following wash-out of the EGF from the culture, the emission ratio decreased in a time-dependent manner, and the decrease was accelerated by the addition of the AG1478 EGFR inhibitor. No response was observed when cells were incubated with the EGFR inhibitor prior to addition of EGF, whereas the Src kinase inhibitor, PP1, had no effect on the increase in emission ratio due to EGF.

Src activity was stimulated in HeLa cells and in NIH3T3 cells with EGF (50 ng/ml) and PDGF (50 ng/ml), respectively. To inhibit Src activity, PP1 (A.G. Scientific) was incubated with the cells at 100 nM for 30 min at room temperature. FRET was measured in the HeLa cells, and a 25% FRET decrease was measured in response to Src activation. The HeLa cells demonstrated membrane ruffling, characteristic of EGF-stimulated cells. A similar FRET decrease occurred in the NIH3T3 cells following administration of PDGF. In both HeLa cells and NIH3T3 cells, the Src inhibitor, PP1, inhibited the FRET response, whereas the EGFR inhibitor, AG1478, had no significant effect.

Biochemical Analysis of the Chimeric EGFR or Src Reporter Proteins Expressed in Mammalian Cells Reporters expressed in mammalian cells were analyzed by immunoprecipitation (IP), western blot analysis, or fluorescence of the purified protein. For IP and western blot analysis, the following procedure was used. Following exposure to the appropriate stimulant or chemical (EGF, PDGF, or inhibitor), transfected cells in 10 cm culture dishes were rinsed twice with ice-cold HBSS (20 mM Hepes, pH 7.4, 2 g/l D-glucose) and lysed with 1.5 ml lysis buffer (50 mM Tris, pH 7.4, 100 mM NaCl, 1 mM EDTA, 0.1% Triton X-100, 10 mM NaF, 2 mM sodium orthovanadate, 1 mM phenylmethylsulfonyl fluoride, 10 μg/ml pepstatin, 10 μg/ml leupeptin, and 10 μg/ml aprotinin). The suspensions were cleared by centrifugation, and the reporters were immunoprecipitated from the supernatant using a rabbit polyclonal anti-GFP antibody immobilized on protein G-Sepharose resin (Amersham). Western blot analysis was performed on samples run in 12% PAGE-SDS gels using a mouse monoclonal anti-phosphotyrosine antibody (Upstate Biotechnology), a rabbit monoclonal anti-EGFR antibody (Calbiochem), or a mouse monoclonal anti-GFP antibody (Clontech) with secondary detection by anti-rabbit HRP or anti-mouse HRP.

For fluorescence analysis of purified reporters, the crude cell lysates were purified over a column of Ni-NTA agarose (Qiagen). The $His_6$-tagged reporters were eluted with 50 mM Tris pH 7.4/300 mM NaCl/100 mM imidazole and dialyzed into 50 mM Tris pH 7.4/50 mM NaCl/10 mM $MgCl_2$.

EXAMPLE 3

Identification of Chimeric Phosphorylation Indicators Using High Throughput Screening Based on the results described Examples 1 and 2, additional chimeric phosphorylation indicators can be developed and optimized, using a variety of fluorescent proteins, luminescent molecules, kinase or phosphatase substrates, PAABDs, and tetracysteine motifs. High throughput strategies are particularly useful for systematically generating and testing diverse libraries of such constructs (Zhao and Arnold, Curr. Opin. Chem. Biol. 3:284–290, 1997, which is incorporated herein by reference).

Initial high throughput diversity generation and screening are performed using the exemplified chimeric phosphorylation indicators (Examples 1 and 2), which are active in mammalian cells. Iterative cycles of variegation, for example (see U.S. Pat. No. 5,837,500, which is incorporated herein by reference), can confer additional useful features on these chimeric reporters. Diversity also can be created by a variety of other methods, including, for example, error prone PCR, oligonucleotide-directed mutagenesis with various degrees of bias towards wild-type codons (Cormack et al., Gene 173:33–38, 1996, which is incorporated herein by reference), DNA shuffling (Crameri et al., Nat. Biotechnol. 14:315–319, 1996; Minshull and Stemmer, Curr. Opin. Chem. Biol. 3:284–290, 1999, each of which is incorporated herein by reference), incorporation of random spacers, or "incremental truncation for the creation of hybrid enzymes" (Ostermeier et al., Nat. Biotechnol. 17:1205–1209, 1999, which is incorporated herein by reference).

High throughput screening can utilize a method such as fluorescence activated cell sorting (FACS), which can allow the identification of mutants or clones with the greatest brightness, highest expression levels under particular growth conditions, or unusual emissions spectra. FACS can be particularly useful for screening FRET constructs, in which the donor and acceptor are part of the same chimera, so that ratios of the two emissions reflect only FRET rather than variable expression levels. Chimeras having the most desirable characteristics then can be examined further to identify those that respond before and after application of a stimulus such as induction of kinase activity in a correlated way.

Although the chimeric phosphorylatable indicators can be screened in bacteria, yeast, or mammalian cells, the latter are preferred because, ultimately, the indicators are most useful for studies of mammalian cells. Standard cultured lines such as HeLa, CHO, HEK-293, 3T3, or Jurkat are the cells of choice for the initial screening studies, although other cells, including cardiomyocytes, B cells, and the like can be used for confirmatory studies. For studies in mammalian cell lines, it is preferred that any individual cell pick up only a single chimeric sequence because the presence of fluorescent but nonresponsive proteins would fatally dilute and obscure the response of the good construct. Transfection methods such as electroporation or lipofection allow many different DNA molecules to enter each permeabilized cell and, therefore, are suitable only for screens in which nonfunctional sequences do not interfere. In comparison, a method such as retroviral infection can allow for insertion of a single chimera construct into the viral package. By working with a multiplicity of infection much less than 1, nearly all the transfectants will contain only a single introduced sequence. Cells that do not get infected will be nonfluorescent and noninterfering.

FACS can be used to discard nonfluorescent cells, and to deposit single fluorescent individuals into separate wells of microtiter plates. The cells then can be expanded so as to obtain a sufficient number of cells in each well, probably with ongoing antibiotic selection. The clones then can be read using a microplate fluorometer, before and after appropriately stimulating the cells, for example by pharmacologically activating an endogenous or coexpressed kinase or phosphatase. Alternatively, the cells can be lysed and the fluorescence read before and after adding a separately expressed and purified enzyme. DNA recovered from the wells showing the best response then can be sequenced and re-expressed.

A microscopy-based method also can be used. For example, a relatively large numbers of cells can be plated into each well of several microtiter plates and, after the cells have attached and physiologically equilibrated to the culture, a reagent can be added to stimulate the cells, which are then be re-imaged and compared to the prestimulus views. Appropriate software can highlight those cells having the greatest response to the stimulus, and a DNA sample can be obtained from the cells using a micropipet. The advantages of this strategy are that that it avoids the low survival-rate and long duration associated with growing clones from single isolated cells, and that much more diverse libraries can be examined, with hundreds to thousands of cells per well.

At least two versions of planar microfluidic cell sorting have been proposed, one using cells pumped single file by electroosmotically driven flow through a T junction molded into silicone elastomer (Fu et al., Nat. Biotechnol. 17:1109–1111, 1999, which is incorporated herein by reference), and the other using arrays of cells individually releasable by microbubble formation. These methods work with nonadherent cells and, in principle, can be used to recover live cells, not just DNA samples.

Although the invention has been described with reference to the above examples, it will be understood that modifications and variations are encompassed within the spirit and scope of the invention. Accordingly, the invention is limited only by the following claims.

What is claimed is:

1. An isolated polynucleotide encoding a chimeric phosphorylation indicator comprising in operative linkage:

a donor molecule comprising an amino acid sequence having at least 80% sequence identity to ECFP (amino acids 1–227 of SEQ ID NO: 6);

a phosphorylatable domain comprising EEEAEYMNMAPQS (SEQ ID NO: 23);

a phosphoaminoacid binding domain comprising a Src homology domain-2; and an acceptor molecule comprising an amino acid sequence having at least 80% sequence identity to YFP (SEQ ID NO: 10), wherein the acceptor molecule has the mutation K69M with respect to SEQ ID NO: 10, and wherein the amino acid following the initiating methionine is assigned the '1 position in the numbering of said donor and acceptor amino acid sequences, and wherein at least one of the donor or acceptor molecules comprising a mutation which corresponds to an A206K mutation, an L221K mutation, an F223R mutation, or an L221K and F223R mutation of SEQ ID NO: 6 or 10, wherein said mutation results in a reduced tendency to oligomerize.

2. The polynucleotide of claim 1, wherein the donor molecule and the acceptor molecule exhibit a detectable resonance energy transfer when the donor is excited.

3. The polynucleotide of claim 1, wherein the donor and the acceptor molecule exhibit a detectable resonance energy transfer when the donor releases energy, and the detectable resonance energy transfer is fluorescence resonance energy transfer.

4. The polynucleotide of claim 1, wherein at least one amino acid of the phosphorylatable domain is phosphorylated.

5. The polynucleotide of claim 4, wherein the amino acid is serine, threonine, tyrosine, or a combination thereof.

6. The polynucleotide of claim 1, which is operatively linked to an expression control sequence.

7. The polynucleotide of claim 6, wherein the expression control sequence is a transcription regulatory element, a translation regulatory element, or a combination thereof.

8. A kit comprising at least one polynucleotide of claim 1.

9. The kit of claim 8, comprising a plurality of polynucleotides encoding a plurality of chimeric phosphorylation indicators comprising at least two chimeric phosphorylation indicators differing from each other in at least one portion selected from the portions consisting of donor molecule, phosphorylatable domain, phosphoaminoacid binding domain, and acceptor molecule.

10. The kit of claim 9, wherein the chimeric phosphorylation indicators encoded by the polynucleotides comprise phosphorylatable domains different from each other.

11. The kit of claim 9, wherein the chimeric phosphorylation indicators encoded by the polynucleotides comprise donor molecules different from each other or acceptor molecules different from each other or both donor and acceptor molecules different from each other.

12. A vector comprising the polynucleotide of claim 1.

13. The vector of claim 12 which is an expression vector.

14. An isolated polynucleotide encoding a chimeric phosphorylation indicator, said indicator comprising:

a phosphorylatable polypeptide; and a fluorescent protein comprising a mutation which corresponds to an A206K mutation, an L221K mutation, an F223R mutation or an L221K and F223R mutation of SEQ ID NOS: 6 or 10, wherein the amino acid following the initiating methionine is assianed the '1 position in the numbering of SEQ ID NOS: 6 and 10, or an A206K mutation, an L221K mutation, an F223R mutation, or an L221K and F223R mutation of SEQ ID NO: 2, wherein said mutation results in a reduced tendency to oligomerize, wherein said polynucleotide is operatively linked to an expression control senuence.

15. The polynucleotide of claim 14, wherein the chimenc phosphorylation indicator further comprising a cell compartmentalization domain.

16. The polynucleotide of claim 15, wherein the cell compartmentalization domain is a membrane translocating domain.

17. The polynucleotide of claim 16, wherein the membrane translocating domain comprising an amino acid sequence CRQIKWFNRRMKWKK (SEQ ID NO:18).

18. The polynucleotide of claim 16, wherein the membrane translocating domain is operatively linked to the fluorescent protein through an amino acid sequence CCXXCC (SEQ ID NO:17) where X is any amino acid.

19. The polynucleotide of claim 14, wherein the phosphorylatable polypeptide comprising a serine/threonine kinase phosphorylatable domain.

20. The polynucleotide of claim 14, wherein the phosphorylatable polypeptide comprising a tyrosine kinase phosphorylatable domain.

21. The polynucleotide of claim 20, encoding a polypeptide comprising, in an orientation from the amino terminus to carboxy terminus, an ECFP (1–227) (amino acids 1 to 227 of SEQ ID NO:6) molecule, an SH2 phosphoaminoacid binding domain from Shc, a GSHSGSGKP (SEQ ID NO:22) linker, a phosphorylatable domain comprising EEEAEYMNMAPQS (SEQ ID NO:23), and citrine.

22. The polynucleotide of claim 14, wherein the expression control sequence is a transcription regulatory element, a translation regulatory element, or a combination thereof.

23. A kit comprising at least one polynucleotide of claim 14.

24. The kit of claim 23, comprising a plurality of polynucleotides encoding a plurality of chimeric phosphorylation indicators comprising at least two chimeric phosphorylation indicators differing from each other in at least one portion selected from the portions consisting of phosphorylatable polypeptide and fluorescent protein.

25. The kit of claim 24, wherein the chimeric phosphorylation indicators encoded by the polynucleotides comprise different phosphorylatable polypeptides.

26. The kit of claim 24, wherein the chimeric phosphorylation indicators encoded by the polynucleotides comprise different fluorescent proteins.

27. A kit comprising at least one polynucleotide of claim 14, which polynucleotide is operatively linked to an expression control sequence, wherein the chimeric phosphorylation indicator further comprising a phosphoamino acid binding domain operatively linked to the phosphorylatable polypeptide, wherein the fluorescent protein comprising an N-terminal portion and a C-terminal portion, and wherein the phosphorylatable polypeptide and operatively linked phosphoaminoacid binding domain is operatively inserted between the N-terminal portion and C-terminal portion of the fluorescent protein.

28. The kit of claim 27, comprising a plurality of chimeric phosphorylation indicators comprising at least two chimeric phosphorylation indicators differing from each other in at least one portion selected from the portions consisting of phosphorylatable polypeptide and fluorescent protein.

29. The kit of claim 28, wherein the chimeric phosphorylation indicators comprise different phosphorylatable polypeptides.

30. The kit of claim 27, wherein the plurality of different chimeric phosphorylation indicators comprise different fluorescent proteins.

* * * * *

SEQUENCE LISTING

```
<160> NUMBER OF SEQ ID NOS: 42

<210> SEQ ID NO 1
<211> LENGTH: 716
<212> TYPE: DNA
<213> ORGANISM: Aequorea victoria
<220> FEATURE:
<221> NAME/KEY: CDS
<222> LOCATION: (1)..(714)

<400> SEQUENCE: 1 atg agt aaa gga gaa gaa ctt ttc act gga gtt gtc cca att ctt gtt      48
Met Ser Lys Gly Glu Glu Leu Phe Thr Gly Val Val Pro Ile Leu Val
1               5                  10                  15 gaa tta gat ggt gat gtt aat ggg cac aaa ttt tct gtc agt gga gag      96
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Glu | Leu | Asp | Gly | Asp | Val | Asn | Gly | His | Lys | Phe | Ser | Val | Ser | Gly | Glu |     |
|     |     |     | 20  |     |     |     | 25  |     |     |     | 30  |     |     |     |     |     |

```
ggt gaa ggt gat gca aca tac gga aaa ctt acc ctt aaa ttt att tgc       144
Gly Glu Gly Asp Ala Thr Tyr Gly Lys Leu Thr Leu Lys Phe Ile Cys
            35                  40                  45 act act gga aaa cta cct gtt cca tgg cca aca ctt gtc act act ttc       192
Thr Thr Gly Lys Leu Pro Val Pro Trp Pro Thr Leu Val Thr Thr Phe
 50                  55                  60 tct tat ggt gtt caa tgc ttt tca aga tac cca gat cat atg aaa cag       240
Ser Tyr Gly Val Gln Cys Phe Ser Arg Tyr Pro Asp His Met Lys Gln
 65                  70                  75                  80 cat gac ttt ttc aag agt gcc atg ccc gaa ggt tat gta cag gaa aga       288
His Asp Phe Phe Lys Ser Ala Met Pro Glu Gly Tyr Val Gln Glu Arg
                 85                  90                  95 act ata ttt ttc aaa gat gac ggg aac tac aag aca cgt gct gaa gtc       336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att       384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac       432
Asp Phe Lys Glu Asp Gly Asn Ile Leu Gly His Lys Leu Glu Tyr Asn
130                 135                 140 tat aac tca cac aat gta tac atc atg gca gac aaa caa aag aat gga       480
Tyr Asn Ser His Asn Val Tyr Ile Met Ala Asp Lys Gln Lys Asn Gly
145                 150                 155                 160 atc aaa gtt aac ttc aaa att aga cac aac att gaa gat gga agc gtt       528
Ile Lys Val Asn Phe Lys Ile Arg His Asn Ile Glu Asp Gly Ser Val
                165                 170                 175 caa cta gca gac cat tat caa caa aat act cca att ggc gat ggc cct       576
Gln Leu Ala Asp His Tyr Gln Gln Asn Thr Pro Ile Gly Asp Gly Pro
            180                 185                 190 gtc ctt tta cca gac aac cat tac ctg tcc aca caa tct gcc ctt tcg       624
Val Leu Leu Pro Asp Asn His Tyr Leu Ser Thr Gln Ser Ala Leu Ser
        195                 200                 205 aaa gat ccc aac gaa aag aga gac cac atg gtc ctt ctt gag ttt gta       672
Lys Asp Pro Asn Glu Lys Arg Asp His Met Val Leu Leu Glu Phe Val
210                 215                 220 aca gct gct ggg att aca cat ggc atg gat gaa cta tac aaa ta            716
Thr Ala Ala Gly Ile Thr His Gly Met Asp Glu Leu Tyr Lys
225                 230                 235

<210> SEQ ID NO 2
<211> LENGTH: 238
<212> TYPE: PRT
<213> ORGANISM: Aequorea victoria

<400> SEQUENCE: 2

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
```

-continued

```
                        85                  90                  95
Thr Ile Phe Phe Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
    210                 215                 220
Thr Ala Ala Gly Ile Thr His Gly Met Asp Glu Leu Tyr Lys
225                 230                 235

<210> SEQ ID NO 3
<211> LENGTH: 720
<212> TYPE: DNA
<213> ORGANISM: Aequorea victoria
<220> FEATURE:
<221> NAME/KEY: CDS
<222> LOCATION: (1)..(720)

<400> SEQUENCE: 3 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160
```

-continued

| | | | | | | | | | | | | | | | |
|---|---|---|---|---|---|---|---|---|---|---|---|---|---|---|---|
| ggc | atc | aag | gtg | aac | ttc | aag | atc | cgc | cac | aac | atc | gag | gac | ggc | agc | 528 |
| Gly | Ile | Lys | Val | Asn | Phe | Lys | Ile | Arg | His | Asn | Ile | Glu | Asp | Gly | Ser | |
| | | | 165 | | | | | 170 | | | | | 175 | | | |

| gtg | cag | ctc | gcc | gac | cac | tac | cag | cag | aac | acc | ccc | atc | ggc | gac | ggc | 576 |
| Val | Gln | Leu | Ala | Asp | His | Tyr | Gln | Gln | Asn | Thr | Pro | Ile | Gly | Asp | Gly |
| | | | 180 | | | | | 185 | | | | | 190 | | | |

| ccc | gtg | ctg | ctg | ccc | gac | aac | cac | tac | ctg | agc | acc | cag | tcc | gcc | ctg | 624 |
| Pro | Val | Leu | Leu | Pro | Asp | Asn | His | Tyr | Leu | Ser | Thr | Gln | Ser | Ala | Leu |
| | | | 195 | | | | | 200 | | | | | 205 | | | |

| agc | aaa | gac | ccc | aac | gag | aag | cgc | gat | cac | atg | gtc | ctg | ctg | gag | ttc | 672 |
| Ser | Lys | Asp | Pro | Asn | Glu | Lys | Arg | Asp | His | Met | Val | Leu | Leu | Glu | Phe |
| | 210 | | | | | 215 | | | | | 220 | | | | | |

| gtg | acc | gcc | gcc | ggg | atc | act | ctc | ggc | atg | gac | gag | ctg | tac | aag | taa | 720 |
| Val | Thr | Ala | Ala | Gly | Ile | Thr | Leu | Gly | Met | Asp | Glu | Leu | Tyr | Lys | |
| 225 | | | | | 230 | | | | | 235 | | | | | | |

<210> SEQ ID NO 4
<211> LENGTH: 239
<212> TYPE: PRT
<213> ORGANISM: Aequorea victoria

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 5
<211> LENGTH: 720
<212> TYPE: DNA
<213> ORGANISM: Aequorea victoria

<220> FEATURE:
<221> NAME/KEY: CDS
<222> LOCATION: (1)..(720)

<400> SEQUENCE: 5

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac agg ttc agc gtg tcc ggc      96
Val Glu Leu Asp Gly Asp Val Asn Gly His Arg Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
    50                  55                  60 ctg acc tgg ggc gtg cag tgc ttc agc cgc tac ccc gac cac atg aag     240
Leu Thr Trp Gly Val Gln Cys Phe Ser Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgt acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac atc agc cac aac gtc tat atc acc gcc gac aag cag aag aac     480
Asn Tyr Ile Ser His Asn Val Tyr Ile Thr Ala Asp Lys Gln Lys Asn
145                 150                 155                 160 ggc atc aag gcc cac ttc aag atc cgc cac aac atc gag gac ggc agc     528
Gly Ile Lys Ala His Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa     720
Val Thr Ala Ala Gly Ile Thr Leu Gly Met Asp Glu Leu Tyr Lys
225                 230                 235
```

<210> SEQ ID NO 6
<211> LENGTH: 239
<212> TYPE: PRT
<213> ORGANISM: Aequorea victoria

<400> SEQUENCE: 6

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30
```

-continued

```
Glu Gly Glu Gly Asp Ala Thr Tyr Gly Lys Leu Thr Leu Lys Phe Ile
         35                  40                  45
Cys Thr Thr Gly Lys Leu Pro Val Pro Trp Pro Thr Leu Val Thr Thr
 50                  55                  60
Leu Thr Trp Gly Val Gln Cys Phe Ser Arg Tyr Pro Asp His Met Lys
 65                  70                  75                  80
Gln His Asp Phe Phe Lys Ser Ala Met Pro Glu Gly Tyr Val Gln Glu
                 85                  90                  95
Arg Thr Ile Phe Phe Lys Asp Asp Gly Asn Tyr Lys Thr Arg Ala Glu
                100                 105                 110
Val Lys Phe Glu Gly Asp Thr Leu Val Asn Arg Ile Glu Leu Lys Gly
            115                 120                 125
Ile Asp Phe Lys Glu Asp Gly Asn Ile Leu Gly His Lys Leu Glu Tyr
130                 135                 140
Asn Tyr Ile Ser His Asn Val Tyr Ile Thr Ala Asp Lys Gln Lys Asn
145                 150                 155                 160
Gly Ile Lys Ala His Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
210                 215                 220
Val Thr Ala Ala Gly Ile Thr Leu Gly Met Asp Glu Leu Tyr Lys
225                 230                 235
```

<210> SEQ ID NO 7
<211> LENGTH: 720
<212> TYPE: DNA
<213> ORGANISM: Aequorea victoria
<220> FEATURE:
<221> NAME/KEY: CDS
<222> LOCATION: (1)..(720)

<400> SEQUENCE: 7

```
atg gtg agc aag ggc gag gag ctg ttc acc ggg gtg gtg ccc atc ctg       48
Met Val Ser Lys Gly Glu Glu Leu Phe Thr Gly Val Val Pro Ile Leu
  1               5                  10                  15 gtc gag ctg gac ggc gac gta aac ggc cac aag ttc agc gtg tcc ggc       96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
 50                  55                  60 ttc ggc tac ggc gtg cag tgc ttc gcc cgc tac ccc gac cac atg aag      240
Phe Gly Tyr Gly Val Gln Cys Phe Ala Arg Tyr Pro Asp His Met Lys
 65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
                100                 105                 110
```

```
gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
        130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg      624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag taa      720
Val Thr Ala Ala Gly Ile Thr Leu Gly Met Asp Glu Leu Tyr Lys
225                 230                 235

<210> SEQ ID NO 8
<211> LENGTH: 239
<212> TYPE: PRT
<213> ORGANISM: Aequorea victoria

<400> SEQUENCE: 8

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205
```

-continued

Ser Lys Asp Pro Asn Glu Lys Arg Asp His Met Val Leu Leu Glu Phe
    210             215                 220

Val Thr Ala Ala Gly Ile Thr Leu Gly Met Asp Glu Leu Tyr Lys
225                 230                 235

<210> SEQ ID NO 9
<211> LENGTH: 720
<212> TYPE: DNA
<213> ORGANISM: Aequorea victoria
<220> FEATURE:
<221> NAME/KEY: CDS
<222> LOCATION: (1)..(720)

<400> SEQUENCE: 9

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
50                  55                  60 ttc ggc tac ggc ctg aag tgc ttc gcc cgc tac ccc gac cac atg aag     240
Phe Gly Tyr Gly Leu Lys Cys Phe Ala Arg Tyr Pro Asp His Met Lys
65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg     624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
210                 215                 220 gtg acc gcc gcc ggg atc act ctc ggc atg gac gag ctg tac aag taa     720
Val Thr Ala Ala Gly Ile Thr Leu Gly Met Asp Glu Leu Tyr Lys
225                 230                 235
```

<210> SEQ ID NO 10

-continued

<210> SEQ ID NO 10
<211> LENGTH: 239
<212> TYPE: PRT
<213> ORGANISM: Aequorea victoria

<400> SEQUENCE: 10

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Lys Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 11
<211> LENGTH: 859
<212> TYPE: DNA
<213> ORGANISM: Discosoma sp.
<220> FEATURE:
<221> NAME/KEY: CDS
<222> LOCATION: (54)..(731)

<400> SEQUENCE: 11
gtttcagcca gtgacggtca gtgacagggt gagccacttg gtataccaac aaa atg         56
                                                            Met
                                                            1 agg tct tcc aag aat gtt atc aag gag ttc atg agg ttt aag gtt cgc        104
Arg Ser Ser Lys Asn Val Ile Lys Glu Phe Met Arg Phe Lys Val Arg
        5                   10                  15 atg gaa gga acg gtc aat ggg cac gag ttt gaa ata gaa ggc gaa gga        152
Met Glu Gly Thr Val Asn Gly His Glu Phe Glu Ile Glu Gly Glu Gly
            20                  25                  30 gag ggg agg cca tac gaa ggc cac aat acc gta aag ctt aag gta acc        200
Glu Gly Arg Pro Tyr Glu Gly His Asn Thr Val Lys Leu Lys Val Thr
        35                  40                  45 aag ggg gga cct ttg cca ttt gct tgg gat att ttg tca cca caa ttt        248
Lys Gly Gly Pro Leu Pro Phe Ala Trp Asp Ile Leu Ser Pro Gln Phe

```
                      50                  55                  60                  65
cag tat gga agc aag gta tat gtc aag cac cct gcc gac ata cca gac              296
Gln Tyr Gly Ser Lys Val Tyr Val Lys His Pro Ala Asp Ile Pro Asp
                 70                  75                  80 tat aaa aag ctg tca ttt cct gaa gga ttt aaa tgg gaa agg gtc atg              344
Tyr Lys Lys Leu Ser Phe Pro Glu Gly Phe Lys Trp Glu Arg Val Met
             85                  90                  95 aac ttt gaa gac ggt ggc gtc gtt act gta acc cag gat tcc agt ttg              392
Asn Phe Glu Asp Gly Gly Val Val Thr Val Thr Gln Asp Ser Ser Leu
             100                 105                 110 cag gat ggc tgt ttc atc tac aag gtc aag ttc att ggc gtg aac ttt              440
Gln Asp Gly Cys Phe Ile Tyr Lys Val Lys Phe Ile Gly Val Asn Phe
         115                 120                 125 cct tcc gat gga cct gtt atg caa aag aag aca atg ggc tgg gaa gcc              488
Pro Ser Asp Gly Pro Val Met Gln Lys Lys Thr Met Gly Trp Glu Ala
130                 135                 140                 145 agc act gag cgt ttg tat cct cgt gat ggc gtg ttg aaa gga gag att              536
Ser Thr Glu Arg Leu Tyr Pro Arg Asp Gly Val Leu Lys Gly Glu Ile
                 150                 155                 160 cat aag gct ctg aag ctg aaa gac ggt ggt cat tac cta gtt gaa ttc              584
His Lys Ala Leu Lys Leu Lys Asp Gly Gly His Tyr Leu Val Glu Phe
             165                 170                 175 aaa agt att tac atg gca aag aag cct gtg cag cta cca ggg tac tac              632
Lys Ser Ile Tyr Met Ala Lys Lys Pro Val Gln Leu Pro Gly Tyr Tyr
             180                 185                 190 tat gtt gac tcc aaa ctg gat ata aca agc cac aac gaa gac tat aca              680
Tyr Val Asp Ser Lys Leu Asp Ile Thr Ser His Asn Glu Asp Tyr Thr
         195                 200                 205 atc gtt gag cag tat gaa aga acc gag gga cgc cac cat ctg ttc ctt              728
Ile Val Glu Gln Tyr Glu Arg Thr Glu Gly Arg His His Leu Phe Leu
210                 215                 220                 225 taa ggctgaactt ggctcagacg tgggtgagcg gtaatgacca caaaaggcag                   781
cgaagaaaaa ccatgatcgt ttttttttagg ttggcagcct gaaatcgtag gaaatacatc           841
agaaatgtta caaacagg                                                          859

<210> SEQ ID NO 12
<211> LENGTH: 225
<212> TYPE: PRT
<213> ORGANISM: Discosoma sp.

<400> SEQUENCE: 12

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125
```

```
Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 13
<211> LENGTH: 18
<212> TYPE: PRT
<213> ORGANISM: Artificial sequence
<220> FEATURE:
<223> OTHER INFORMATION: Synthetic peptide

<400> SEQUENCE: 13

Gly Ser Thr Ser Gly Ser Gly Lys Pro Gly Ser Gly Glu Gly Ser Thr
1               5                   10                  15

Lys Gly

<210> SEQ ID NO 14
<211> LENGTH: 8
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (2)..(2)
<223> OTHER INFORMATION: Phosphorylated peptide

<400> SEQUENCE: 14

Asp Tyr Ile Ile Pro Leu Pro Asp
1               5

<210> SEQ ID NO 15
<211> LENGTH: 9
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (8)..(8)
<223> OTHER INFORMATION: Phosphorylated peptide

<400> SEQUENCE: 15

His Ile Ile Glu Asn Pro Gln Tyr Phe
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (5)..(5)
<223> OTHER INFORMATION: Phosphorylated peptide
```

```
<400> SEQUENCE: 16

Ala Arg Ser His Ser Tyr Pro Ala
1               5

<210> SEQ ID NO 17
<211> LENGTH: 6
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (3)..(4)
<223> OTHER INFORMATION: Xaa is any Amino Acid

<400> SEQUENCE: 17

Cys Cys Xaa Xaa Cys Cys
1               5

<210> SEQ ID NO 18
<211> LENGTH: 15
<212> TYPE: PRT
<213> ORGANISM: Artificial sequence
<220> FEATURE:
<223> OTHER INFORMATION: Synthetic peptide

<400> SEQUENCE: 18

Cys Arg Gln Ile Lys Trp Phe Asn Arg Arg Met Lys Trp Lys Lys
1               5                   10                  15

<210> SEQ ID NO 19
<211> LENGTH: 7
<212> TYPE: PRT
<213> ORGANISM: Artificial sequence
<220> FEATURE:
<223> OTHER INFORMATION: Synthetic peptide

<400> SEQUENCE: 19

Ala Gly Gly Thr Gly Gly Ser
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic peptide

<400> SEQUENCE: 20

Leu Arg Arg Ala Ser Leu Pro
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic peptide

<400> SEQUENCE: 21

Gly Gly Thr Gly Gly Ser Glu Leu
1               5

<210> SEQ ID NO 22
<211> LENGTH: 9
<212> TYPE: PRT
<213> ORGANISM: Artificial sequence
```

```
<220> FEATURE:
<223> OTHER INFORMATION: Synthetic peptide

<400> SEQUENCE: 22

Gly Ser His Ser Gly Ser Gly Lys Pro
1               5

<210> SEQ ID NO 23
<211> LENGTH: 13
<212> TYPE: PRT
<213> ORGANISM: Artificial sequence
<220> FEATURE:
<223> OTHER INFORMATION: Synthetic peptide

<400> SEQUENCE: 23

Glu Glu Glu Ala Glu Tyr Met Asn Met Ala Pro Gln Ser
1               5                   10

<210> SEQ ID NO 24
<211> LENGTH: 15
<212> TYPE: PRT
<213> ORGANISM: Artificial sequence
<220> FEATURE:
<223> OTHER INFORMATION: Synthetic peptide

<400> SEQUENCE: 24

Gly Ser Thr Ser Gly Ser Gly Lys Pro Gly Ser Gly Glu Gly Ser
1               5                   10                  15

<210> SEQ ID NO 25
<211> LENGTH: 6
<212> TYPE: PRT
<213> ORGANISM: Artificial sequence
<220> FEATURE:
<223> OTHER INFORMATION: Synthetic peptide

<400> SEQUENCE: 25

Glu Ile Tyr Gly Glu Phe
1               5

<210> SEQ ID NO 26
<211> LENGTH: 34
<212> TYPE: DNA
<213> ORGANISM: Artificial sequence
<220> FEATURE:
<223> OTHER INFORMATION: Forward primer for PCR

<400> SEQUENCE: 26
gggcatgcat atggagaaga ctgagctgat ccag                           34

<210> SEQ ID NO 27
<211> LENGTH: 92
<212> TYPE: DNA
<213> ORGANISM: Artificial sequence
<220> FEATURE:
<223> OTHER INFORMATION: Reverse primer for PCR

<400> SEQUENCE: 27
cgcggagctc gctgccgccg gtgccgccca ggctggcgcg acggaggctg ccgccggtgc    60
cgcctgcaga gtctgatgtc caaagtgtta gg                                 92

<210> SEQ ID NO 28
<211> LENGTH: 33
<212> TYPE: DNA
<213> ORGANISM: Artificial sequence
<220> FEATURE:
```

<223> OTHER INFORMATION: Primer for PCR

<400> SEQUENCE: 28
cgtcgcgcca gcctgccagg caccggcggc agc       33

<210> SEQ ID NO 29
<211> LENGTH: 33
<212> TYPE: DNA
<213> ORGANISM: Artificial sequence
<220> FEATURE:
<223> OTHER INFORMATION: Primer for PCR

<400> SEQUENCE: 29
gctgccgccg gtggctggca ggctggcgcg acg       33

<210> SEQ ID NO 30
<211> LENGTH: 32
<212> TYPE: DNA
<213> ORGANISM: Artificial sequence
<220> FEATURE:
<223> OTHER INFORMATION: Primer for PCR

<400> SEQUENCE: 30
gcctccgtcg cgccgcactg ccaggcaccg gc        32

<210> SEQ ID NO 31
<211> LENGTH: 32
<212> TYPE: DNA
<213> ORGANISM: Artificial sequence
<220> FEATURE:
<223> OTHER INFORMATION: Primer for PCR

<400> SEQUENCE: 31
gccggtgcct ggcagtgcgg cgcgacggag gc        32

<210> SEQ ID NO 32
<211> LENGTH: 7
<212> TYPE: PRT
<213> ORGANISM: Artificial sequence
<220> FEATURE:
<223> OTHER INFORMATION: Synthetic peptide

<400> SEQUENCE: 32

Leu Arg Arg Ala Ser Leu Gly
1               5

<210> SEQ ID NO 33
<211> LENGTH: 9
<212> TYPE: PRT
<213> ORGANISM: Artificial sequence
<220> FEATURE:
<223> OTHER INFORMATION: Synthetic peptide

<400> SEQUENCE: 33

Ala Gln Arg Ser Thr Ser Thr Pro Asn
1               5

<210> SEQ ID NO 34
<211> LENGTH: 6
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (1)..(6)
<223> OTHER INFORMATION: Xaa is any Animo Acid

```
<400> SEQUENCE: 34

Arg Ser Xaa Ser Xaa Pro
1               5

<210> SEQ ID NO 35
<211> LENGTH: 4
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (3)..(3)
<223> OTHER INFORMATION: Xaa is any Amino Acid

<400> SEQUENCE: 35

Arg Arg Xaa Ser
1

<210> SEQ ID NO 36
<211> LENGTH: 4
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (2)..(3)
<223> OTHER INFORMATION: Xaa is any Amino Acid
<221> NAME/KEY: VARIANT
<222> LOCATION: (4)..(4)
<223> OTHER INFORMATION: Xaa is Serine or Threonine

<400> SEQUENCE: 36

Arg Xaa Xaa Xaa
1

<210> SEQ ID NO 37
<211> LENGTH: 4
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (1)..(1)
<223> OTHER INFORMATION: Xaa is Lysine or Arginine
<221> NAME/KEY: VARIANT
<222> LOCATION: (2)..(3)
<223> OTHER INFORMATION: Xaa is any Amino Acid
<221> NAME/KEY: VARIANT
<222> LOCATION: (4)..(4)
<223> OTHER INFORMATION: Xaa is Serine or Threonine

<400> SEQUENCE: 37

Xaa Xaa Xaa Xaa
1

<210> SEQ ID NO 38
<211> LENGTH: 39
<212> TYPE: DNA
<213> ORGANISM: Artificial sequence
<220> FEATURE:
<223> OTHER INFORMATION: Forward primer for PCR

<400> SEQUENCE: 38
gccgcccgca tgcattggtt ccacgggaag ctgagccgg                    39

<210> SEQ ID NO 39
<211> LENGTH: 99
<212> TYPE: DNA
<213> ORGANISM: Artificial sequence
```

```
<220> FEATURE:
<223> OTHER INFORMATION: Reverse primer for PCR

<400> SEQUENCE: 39
taccatgagc tctgattgcg gagccatgtt catgtactca gcttcctctt caggcttccc    60
agatccagag tgagacccca cgggttgctc taggcacag                           99

<210> SEQ ID NO 40
<211> LENGTH: 35
<212> TYPE: DNA
<213> ORGANISM: Artificial sequence
<220> FEATURE:
<223> OTHER INFORMATION: Forward primer for PCR

<400> SEQUENCE: 40
gccgctcgca tgcattggta ttttgggaag atcac                               35

<210> SEQ ID NO 41
<211> LENGTH: 93
<212> TYPE: DNA
<213> ORGANISM: Artificial sequence
<220> FEATURE:
<223> OTHER INFORMATION: Reverse primer for PCR

<400> SEQUENCE: 41
caccatgagc tcaaattcac cgtagatctc agaaccctca ccagaacccg gcttcccaga    60
tccagatgta gacccacaga cgttagtcag gcg                                 93

<210> SEQ ID NO 42
<211> LENGTH: 7
<212> TYPE: PRT
<213> ORGANISM: Artificial sequence
<220> FEATURE:
<223> OTHER INFORMATION: Synthetic peptide
<221> NAME/KEY: VARIANT
<222> LOCATION: (2)..(2)
<223> OTHER INFORMATION: Xaa is Arginine or Lysine
<221> NAME/KEY: VARIANT
<222> LOCATION: (3)..(3)
<223> OTHER INFORMATION: Xaa is Phenylalanine, Arginine, Serine or
      Asparagine
<221> NAME/KEY: VARIANT
<222> LOCATION: (4)..(4)
<223> OTHER INFORMATION: Xaa is Arginine, Histidine, Lysine
<221> NAME/KEY: VARIANT
<222> LOCATION: (5)..(5)
<223> OTHER INFORMATION: Phosphorylated peptide
<221> NAME/KEY: VARIANT
<222> LOCATION: (6)..(6)
<223> OTHER INFORMATION: Xaa is Tryptophan, Tyrosine, Phenylalanine,
      Leucine

<400> SEQUENCE: 42

Arg Xaa Xaa Xaa Ser Xaa Pro
1               5
```